US010604764B2

(12) United States Patent
Rathore et al.

(10) Patent No.: US 10,604,764 B2
(45) Date of Patent: Mar. 31, 2020

(54) COTTON TRANSGENIC EVENT TAM66274

(71) Applicant: The Texas A&M University System, College Station, TX (US)

(72) Inventors: Keerti S. Rathore, College Station, TX (US); Devendra Pandeya, College Station, TX (US); LeAnne M. Campbell, College Station, TX (US); Sreenath R. Palle, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/030,593

(22) Filed: Jul. 9, 2018

(65) Prior Publication Data

US 2019/0008113 A1 Jan. 10, 2019

Related U.S. Application Data

(60) Provisional application No. 62/530,740, filed on Jul. 10, 2017.

(51) Int. Cl.
*C12N 15/113* (2010.01)
*C12N 15/82* (2006.01)
*C12N 9/88* (2006.01)

(52) U.S. Cl.
CPC ........... *C12N 15/8243* (2013.01); *C12N 9/88* (2013.01); *C12N 15/8218* (2013.01); *C12Y 402/03013* (2013.01)

(58) Field of Classification Search
None
See application file for complete search history.

(56) References Cited

U.S. PATENT DOCUMENTS 7,626,081 B2 12/2009 Rathore et al.
8,987,554 B2 * 3/2015 Rathore ............. C12N 15/8243 800/285
2015/0232869 A1 8/2015 Rathore et al.

FOREIGN PATENT DOCUMENTS

WO 2007/019616 A2 2/2007

OTHER PUBLICATIONS

An, et al., "Binary Vectors," in: Plant Molecular Biology Manual (Gelvin and Schilperoort, Eds.) Kluwer Academic Publishers: Dordrecht, The Netherlands A3, Mar. 1-Mar. 19, 1988.
An, et al., "New Cloning Vehicles for Transformation of Higher Plants," The EMBO Journal 4(2):277-284 (1985).
Barker, et al., "Nucleotide Sequence of the T-DNA Region From the Agrobacterium tumefaciens octopine Ti Plasmid pTi15955," Plant Molecular Biology 2(6):335-350 (1983).
Beck, et al., "Nucleotide Sequence and Exact Localization of the Neomycin Phosphotransferase Gene From Transposon Tn5," Gene 19(3):327-336 (1982).
Chen, et al., "Cloning and Heterologous Expression of a Second (+)-δ-Cadinene Synthase From Gossypium arboreum," Journal of Natural Products 59(10):944-951 (1996).
Chen, et al., "Cloning, Expression, and Characterization of (+)-delta-cadinene Synthase: A Catalyst for Cotton Phytoalexin Biosynthesis," Archives of Biochemistry and Biophysics 324(2):255-266 (1995).
Fraley, et al., "Genetic Transformation in Higher Plants," Critical Reviews in Plant Sciences 4(1):I-46 (1986). (Submitted in three parts; pp. (One) 1-14; (Two) 15-23; (Three) 23-46.).
Gleave, "A Versatile Binary Vector System With a T-DNA Organizational-Structure Conducive to Efficient Integration of Cloned DNA Into the Plant Genome," Plant Molecular Biology 20(6):1203-1207 (1992).
International Search Report and Written Opinion regarding International Application No. PCT/US18/41288, dated Nov. 26, 2018.
Li, et al., "Genome Sequence of Cultivated Upland Cotton (*Gossypium hirsutum* TM-1) Provides Insights Into Genome Evolution," Nature Biotechnology 33(5):524-530 (2015).
McMichael, "Combined Effects of the Glandless Genes gI2 and gI3 on Pigment Glands in the Cotton Plant," Agronomy Journal 52(7):385-386 (1960).
McMichael, "Hopi cotton, a Source of Cottonseed Free of Gossypol Pigments," Agronomy Journal 51:630 (1959).
Palle, et al., "RNAi-mediated Ultra-low Gossypol Cottonseed Trait: Performance of Transgenic Lines Under Field Conditions," Plant Biotechnology Journal 11(3):296-304 (2013).
Rathore, et al., "RNAi-mediated, Selective and Substantial Reduction in Gossypol Levels From Cottonseed to Enhance its Food and Feed Value," Proceedings of World Cotton Conference (WCRC-4), Sep. 10-14, Lubbock, TX (2007).
Rathore, et al., "Ultra-low Gossypol Cottonseed: Generational Stability of the Seed-specific, RNAi-mediated Phenotype and Resumption of Terpenoid Profile Following Seed Germination," Plant Biotechnology Journal 10(2):174-183 (2012).
Sunilkumar, et al., "Cotton α-globulin Promoter: Isolation and Functional Characterization in Transgenic Cotton, *Arabidopsis*, and Tobacco," Transgenic Research 11(4):347-359 (2002).
Sunilkumar, et al., "Engineering Cottonseed for Use in Human Nutrition by Tissue Specific Reduction of Toxic Gossypol," Proceedings of the National Academy of Sciences of the United States of America 103(48):18054-18059 (2006).
Tan, et al., "Expression Pattern of (+)-delta-cadinene Synthase Genes and Biosynthesis of Sesquiterpene Aldehydes in Plants of *Gossypium arboreum* L.," Planta 210(4):644-651 (2000).

(Continued)

*Primary Examiner* — Charles Logsdon
(74) *Attorney, Agent, or Firm* — Dentons US LLP

(57) ABSTRACT

The invention provides cotton event TAM66274, and plants, plant cells, seeds, plant parts, and commodity products comprising event TAM66274. The invention also provides polynucleotides specific for event TAM66274 and plants, plant cells, seeds, plant parts, and commodity products comprising polynucleotides specific for event TAM66274. The invention also provides methods related to event TAM66274.

17 Claims, 9 Drawing Sheets

Specification includes a Sequence Listing.

(56) References Cited

OTHER PUBLICATIONS

Townsend, et al., "Antisense Suppression of a (+)-delta-cadinene Synthase Gene in Cotton Prevents the Induction of This Defense Response Gene During Bacterial Blight Infection But Not its Constitutive Expression," Plant Physiology 138:516-528 (2005).

Wang, et al., "Right 25 bp Terminus Sequence of the Nopaline T-DNA is Essential for and Determines Direction of DNA Transfer From Agrobacterium to the Plant Genome," Cell 38(2):455-462 (1984).

Wang, et al., "Site-specific Nick in the T-DNA Border Sequence as a Result of Agrobacterium vir Gene Expression," Science 235(4788):587-591 (1987).

Wesley, et al., "Construct Design for Efficient, Effective and High-throughput Gene Silencing in Plants," Plant Journal 27(6):581-590, (2001).

* cited by examiner

SEQUENCE LISTING

```
<160> NUMBER OF SEQ ID NOS: 12

<210> SEQ ID NO 1
<211> LENGTH: 400
<212> TYPE: DNA
<213> ORGANISM: Artificial sequence
<220> FEATURE:
<223> OTHER INFORMATION: RB transgene insertion junction containing
      flanking genomic and T-DNA insert sequence

<400> SEQUENCE: 1

gtatctggta ctcaaactca cctgagtaac atagattcca tccttattca tacattgccg     60

ctgcattaaa ctgttctgct acactttttc ctgttcattg aagcattacg gatttactga    120

tctattgttt tctagtgtaa tatgtgatag ctgagaagtt ctttgcttta gaggcttcca    180

ttttactttt gtttttgtgg actgatagtt taaactgaag gcgggaaacg acaatctgat    240

catgagcgga gaattaaggg agtcacgtta tgacccccgc cgatgacgcg ggacaagccg    300

ttttacgttt ggaactgaca gaaccgcaac gttgaaggag ccactcagcc ccaatacgca    360
```

aaccgcctct ccccgcgcgt tggccgattc attaatgcag 400

<210> SEQ ID NO 2
<211> LENGTH: 400
<212> TYPE: DNA
<213> ORGANISM: Artificial sequence
<220> FEATURE:
<223> OTHER INFORMATION: LB transgene insertion junction containing
flanking genomic and T-DNA insert sequence

<400> SEQUENCE: 2
gacgttattt atgagatggg tttttatgat tagagtcccg caattataca tttaatacgc 60
gatagaaaac aaaatatagc gcgcaaacta ggataaatta tcgcgcgcgg tgtcatctat 120
gttactagat cgaattaatt cagtacatta aaaacgtccg caatgtgtta ttaagttgtc 180
taagcgtcaa tttgtttaca ttttggattc ttgcagtcac gttaatataa tttcttggaa 240
ctacattttt tccaaaacct atttgctcaa tttggtaaca aagaagcctc cttgtactaa 300
taataaaaat aaaaaaaggc tagctttctg gtattgctta aacatgaaat gtctaaccca 360
tagagcactt gatagatgct tagtacatca aactttcttt 400

<210> SEQ ID NO 3
<211> LENGTH: 7114
<212> TYPE: DNA
<213> ORGANISM: Artificial sequence
<220> FEATURE:
<223> OTHER INFORMATION: Artificial sequence containing the full insert
sequence and flanking genomic sequence

<400> SEQUENCE: 3
gtatctggta ctcaaactca cctgagtaac atagattcca tccttattca tacattgccg 60
ctgcattaaa ctgttctgct acactttttc ctgttcattg aagcattacg gatttactga 120
tctattgttt tctagtgtaa tatgtgatag ctgagaagtt ctttgcttta gaggcttcca 180
ttttactttt gtttttgtgg actgatagtt taaactgaag gcgggaaacg acaatctgat 240
catgagcgga gaattaaggg agtcacgtta tgacccccgc cgatgacgcg ggacaagccg 300
ttttacgttt ggaactgaca gaaccgcaac gttgaaggag ccactcagcc ccaatacgca 360
aaccgcctct ccccgcgcgt tggccgattc attaatgcag ctggcacgac aggtttcccg 420
actggaaagc gggcagtgag cgcaacgcaa ttaatgtgag ttagctcact cattaggcac 480
cccaggcttt acactttatg cttccggctc gtatgttgtg tggaattgtg agcggataac 540
aatttcacac aggaaacagc tatgaccatg attacgccaa gctatttagg tgacactata 600
gaatactcaa gctatgcatc caacgcgttg ggagctctcc catatcgacc tgcaggcggc 660
cgcactagta agctagcttg catgcctgca ggtcctgctg agcctcgaca tgttgtcgca 720
aaattcgccc tggacccgcc caacgatttg tcgtcactgt caaggtttga cctgcacttc 780
atttggggcc cacatacacc aaaaaaaatgc tgcataattc tcggggcagc aagtcggtta 840
cccggccgcc gtgctggacc gggttgaatg gtgcccgtaa ctttcggtag agcggacggc 900
caatactcaa cttcaaggaa tctcacccat gcgcgccggc ggggaaccgg agttcccttc 960
agtgagcgtt attagttcgc cgctcggtgt gtcgtagata ctagcccctg gggcactttt 1020
gaaatttgaa taagatttat gtaatcagtc ttttaggttt gaccggttct gccgcttttt 1080
ttaaaattgg atttgtaata ataaaacgca attgtttgtt attgtggcgc tctatcatag 1140
atgtcgctat aaacctattc agcacaatat attgttttca ttttaatatt gtacatataa 1200
gtagtagggt acaatcagta aattgaacgg agaatattat tcataaaaat acgatagtaa 1260

```
cgggtgatat attcattaga atgaaccgaa accggcggta aggatctgag ctacacatgc   1320
tcaggttttt tacaacgtgc acaacagaat tgaaagcaaa tatcatgcga tcataggcgt   1380
ctcgcatatc tcattaaagc aggactctag tcgagatgcc gagaacgacc tctacaccac   1440
atcccttcga ttccgattac tccgagagca tggattcaat gtttcatgcg acgtattcaa   1500
caagtttaaa gacgagcaag ggaatttcaa gtcatccgtg acaagcgatg ttcgaggatt   1560
gttggaactt taccaagctt cctatttgag ggttcatggg gaagatatat tggatgaagc   1620
aatttctttc accaccaacc atttaagcct tgcagtagca tctttggact atccgttatc   1680
cgaagaggtt tcacatgctt tgaaacaatc aattcgaaga ggcttgccaa gggttgaggc   1740
aagacactat ctttcagtat accaagatat tgagtcccat aataaggttt tgttggagtt   1800
tgctaagatc gatttcaaca tggtacaact tttgcatagg aaagagctaa gtgagatttc   1860
taggtggtgg aaggatttag actttcaaag aaagttgcca tacgcaagag atagagtggt   1920
tgaaggctat ttttggatct caggagtgta ctttgagccc caatattctc ttggtagaaa   1980
gatgttgaca aaagtgatag ccatggcttc tattgtggag gatccaagct tatcgatttc   2040
gaacccagct tcccaactgt aatcaatcca aatgtaagat caatgataac acaatgacat   2100
gatctatcat gttaccttgt ttattcatgt tcgactaatt catttaatta atagtcaatc   2160
catttagaag ttaataaaac tacaagtatt atttagaaat taataagaat gttgattgaa   2220
aaataatact atataaaatt gatagatctt gcgctttgtt atattagcat tagattatgt   2280
tttgttacat tagattactg tttctattag tttgatatta tttgttactt tagcttgtta   2340
tttaatattt tgtttattga taaattacaa gcagattgga atttctaaca aaatatttat   2400
taacttttaa actaaaatat ttagtaatgg tatagatatt taattatata ataaactatt   2460
aatcataaaa aaatattatt ttaatttatt tattcttatt tttactatag tattttatca   2520
ttgatattta attcatcaaa ccagctagaa ttactattat gattaaaaca aatattaatg   2580
ctagtatatc atcttacatg ttcgatcaaa ttcattaaaa ataatatact tactctcaac   2640
ttttatcttc ttcgtcttac acatcacttg tcatattttt ttacattact atgttgttta   2700
tgtaaacaat atatttataa attatttttt cacaattata acaactatat tattataatc   2760
atactaatta acatcactta actattttat actaaaagga aaaaagaaaa taattatttc   2820
cttaccaagc tggggtaccg aattcggatc ctccacaata gaagccatgg ctatcacttt   2880
tgtcaacatc tttctaccaa gagaatattg gggctcaaag tacactcctg agatccaaaa   2940
atagccttca accactctat ctcttgcgta tggcaacttt ctttgaaagt ctaaatcctt   3000
ccaccaccta gaaatctcac ttagctcttt cctatgcaaa agttgtacca tgttgaaatc   3060
gatcttagca aactccaaca aaaccttatt atgggactca atatcttggt atactgaaag   3120
atagtgtctt gcctcaaccc ttggcaagcc tcttcgaatt gattgtttca aagcatgtga   3180
aacctcttcg gataacggat agtccaaaga tgctactgca aggcttaaat ggttggtggt   3240
gaaagaaatt gcttcatcca atatatcttc cccatgaacc ctcaaatagg aagcttggta   3300
aagttccaac aatcctcgaa catcgcttgt cacggatgac ttgaaattcc cttgctcgtc   3360
tttaaacttg ttgaatacgt cgcatgaaac attgaatcca tgctctcgga gtaatcggaa   3420
tcgaagggat gtggtgtaga ggtcgttctc ggcatctcga gcggccgcca gtgtgatgga   3480
tatctgcaga attcggcttg ggacgcgtat cgattacgat aagctctgta ttttgttact   3540
gtgtgatggt aatagcaaag agtggtaatg tatttataga aggtggagct gtggaaggtg   3600
```

-continued

```
atatttttgc atgcaaatct tcatcaacgt gttgaagaca ttgacatgca agatgacgag   3660
tgtgcaaatt aaagaagacg aaatattgtc tctttttttt tttttttgta tagtggtggg   3720
tagatatcga gatgccacat cccttcacat ggtactagca aggttcggac aaactttgtt   3780
gcaggggggt tcatggttgc atctgtaact ggaaggggcg aaatgatgat gctttaacag   3840
cagaaagatg atggaccgtg ttgtgttgta tgtgaactca gttgaattca aagagtgttg   3900
aaactgggaa gggttttaaa gtgagacaga gatgtcccga ttcactgagt taagggttga   3960
gttgatagag gacaagtcaa gtgtacacat gttgctgtgc atggtgatga tctatgagtt   4020
gcaggagata tgaacaaatt cagatatgta tacttttggt atcctgtacg tttgatgctc   4080
atacaaatta gtcctttcaa agtttgaggt atttttattc tttttcaata atattatcta   4140
agtattacat attatatcat tatataaatt tatataataa gaatggaaaa taaaatgttt   4200
cactaaaaac gcttaaaagt aaggatttgg attcaatata gataatagta tataagttat   4260
acagtccaat ctaacataag gtgccacgta ttaagaaata tggtaattta tttttttcata  4320
aattttaaat taattatact atttattaat aattttatat aatcctaaca atatattata   4380
ctatgttagt ttattaaaaa caaacaagta ggcgaggggc tagggccatg actctttaat   4440
tttagggtaa tctataaaaa tagtcatttt tgtttgcctc aggttatatt ttaatcattt   4500
atgtttgaaa tgttacactt tagtcacttt tgttattatt ttgttacaaa gtgatcactc   4560
taccgttaag ctccgttatc tctctaacga taatcctaca tggcagtcca actaaatttt   4620
aggtgtcaac ttggatttct aaataggatg aaaatagctg caggcatgca agcttaagcc   4680
gaattccagc acactggcgg ccgttactag tgatatcccg cggccatggc ggccgggagc   4740
atgcgacgtc gggcccaatt cgccctatag tgagtcgtat tacaattcac tggccgtcgt   4800
tttacaacgt cgtgactggg aaaaccctgg cgttacccaa cttaatcgcc ttgcagcaca   4860
tccccctttc gccagctggc gtaatagcga agaggcccgc accgatcgcc cttcccaaca   4920
gttgcgcagc ctgaatggcg aatggaaatt gtaagcgtta atgggtttct ggagtttaat   4980
gagctaagca catacgtcag aaaccattat tgcgcgttca aaagtcgcct aaggtcacta   5040
tcagctagca aatatttctt gtcaaaaatg ctccactgac gttccataaa ttcccctcgg   5100
tatccaatta gagtctcata ttcactctca atccaaataa tctgcaatgg caattacctt   5160
atccgcaact tctttaccta tttccgcccg gatccgggca ggttctccgg ccgcttgggt   5220
ggagaggcta ttcggctatg actgggcaca acagacaatc ggctgctctg atgccgccgt   5280
gttccggctg tcagcgcagg ggcgcccggt tctttttgtc aagaccgacc tgtccggtgc   5340
cctgaatgaa ctgcaggacg aggcagcgcg gctatcgtgg ctggccacga cgggcgttcc   5400
ttgcgcagct gtgctcgacg ttgtcactga agcgggaagg gactggctgc tattgggcga   5460
agtgccgggg caggatctcc tgtcatctca ccttgctcct gccgagaaag tatccatcat   5520
ggctgatgca atgcggcggc tgcatacgct tgatccggct acctgcccat tcgaccacca   5580
agcgaaacat cgcatcgagc gagcacgtac tcggatggaa gccggtcttg tcgatcagga   5640
tgatctggac gaagagcatc aggggctcgc gccagccgaa ctgttcgcca ggctcaaggc   5700
gcgcatgccc gacggcgagg atctcgtcgt gacccatggc gatgcctgct tgccgaatat   5760
catggtggaa aatggccgct tttctggatt catcgactgt ggccggctgg gtgtggcgga   5820
ccgctatcag gacatagcgt tggctacccg tgatattgct gaagagcttg gcggcgaatg   5880
ggctgaccgc ttcctcgtgc tttacggtat cgccgctccc gattcgcagc gcatcgcctt   5940
ctatcgcctt cttgacgagt tcttctgagc gggactctgg ggttcgaaat gaccgaccaa   6000
```

```
gcgacgccca acctgccatc acgagatttc gattccaccg ccgccttcta tgaaaggttg   6060

ggcttcggaa tcgttttccg ggacgccggc tggatgatcc tccagcgcgg ggatctcatg   6120

ctggagttct tcgcccaccc cgatccaaca cttacgtttg caacgtccaa gagcaaatag   6180

accacgaacg ccggaaggtt gccgcagcgt gtggattgcg tctcaattct ctcttgcagg   6240

aatgcaatga tgaatatgat actgactatg aaactttgag ggaatactgc ctagcaccgt   6300

cacctcataa cgtgcatcat gcatgccctg acaacatgga acatcgctat ttttctgaag   6360

aattatgctc gttggaggat gtcgcggcaa ttgcagctat tgccaaaatc gaaatacccc   6420

tcacgcatgc attcatcaat attattcatg cggggaaagg caagattaat ccaactggca   6480

aatcatccag cgtgattggt aacttcagtt ccagcgactt gattcgtttt ggtgctaccc   6540

acgttttcaa taaggacgag atggtggagt aaagaaggag tgcgtcgaag cagatcgttc   6600

aaacatttgg caataaagtt tcttaagatt gaatcctgtt gccggtcttg cgatgattat   6660

catataattt ctgttgaatt acgttaagca tgtaataatt aacatgtaat gcatgacgtt   6720

atttatgaga tgggttttta tgattagagt cccgcaatta tacatttaat acgcgataga   6780

aaacaaaata tagcgcgcaa actaggataa attatcgcgc gcggtgtcat ctatgttact   6840

agatcgaatt aattcagtac attaaaaacg tccgcaatgt gttattaagt tgtctaagcg   6900

tcaatttgtt tacattttgg attcttgcag tcacgttaat ataatttctt ggaactacat   6960

tttttccaaa acctatttgc tcaatttggt aacaaagaag cctccttgta ctaataataa   7020

aaataaaaaa aggctagctt tctggtattg cttaaacatg aaatgtctaa cccatagagc   7080

acttgataga tgcttagtac atcaaacttt cttt                               7114
```

<210> SEQ ID NO 4
<211> LENGTH: 8901
<212> TYPE: DNA
<213> ORGANISM: Artificial sequence
<220> FEATURE:
<223> OTHER INFORMATION: Artificial sequence containing the full insert sequence and flanking genomic sequence

<400> SEQUENCE: 4

```
gtgcagctat gtttgctcca atggtcaatc cttatgattc actgatgaat aggggagaaa     60

gatatggaat ctgggaaaag tggactcgga aaaggaaatt tatgtatttt ttggctcgaa    120

gatttcctaa atttctatct tacttctacc ggcaaagctt cctctctgga aagcatggtc    180

agattgatca atggctagca ttgacactgg gaagaagggt gagtgatttt ctacactatg    240

agctctctaa ggttccggaa tccagttaag tacagtgcat aatatgcaat tttttgtttc    300

caaggcactc tacggtctta aatgtggaaa tgcataatat tctaagcgag ttactagatt    360

tttgcagcat ttcacttgtc aagcatcgaa tctaaattca tatattgtct ttacaggata    420

gagctttgat agaagaccct atctatgaag aattctggca aagggatgtc gaagaatcaa    480

tccgacaagg aaatgcaaaa ccttttgtgg aggaagctgt attgcaagtt tctaattggg    540

gattcagcct tgcagacctc aaattacaga agaaacagag aggaaaagga atcctaaatt    600

tgatcaagtt ttttcttagt ggctctgagg aagaatatac tggttttctt ggtccaatac    660

acatatggca ggtataattt catcctatgt tgctgtgact cttccatttt cttgaactac    720

tcgtatcttt cacttgtgtc caacacatat ctagacatat gatccttcaa agaccctcca    780

attacatgga aaaacttgtt aaagaaaaag aacataccta tgttggaatg gacctgtatc    840

tggtactcaa actcacctga gtaacataga ttccatcctt attcatacat tgccgctgca    900
```

```
ttaaactgtt ctgctacact ttttcctgtt cattgaagca ttacggattt actgatctat    960
tgttttctag tgtaatatgt gatagctgag aagttctttg ctttagaggc ttccatttta   1020
cttttgtttt tgtggactga tagtttaaac tgaaggcggg aaacgacaat ctgatcatga   1080
gcggagaatt aagggagtca cgttatgacc cccgccgatg acgcgggaca agccgtttta   1140
cgtttggaac tgacagaacc gcaacgttga aggagccact cagccccaat acgcaaaccg   1200
cctctccccg cgcgttggcc gattcattaa tgcagctggc acgacaggtt tcccgactgg   1260
aaagcgggca gtgagcgcaa cgcaattaat gtgagttagc tcactcatta ggcaccccag   1320
gctttacact ttatgcttcc ggctcgtatg ttgtgtggaa ttgtgagcgg ataacaattt   1380
cacacaggaa acagctatga ccatgattac gccaagctat ttaggtgaca ctatagaata   1440
ctcaagctat gcatccaacg cgttgggagc tctcccatat cgacctgcag gcggccgcac   1500
tagtaagcta gcttgcatgc ctgcaggtcc tgctgagcct cgacatgttg tcgcaaaatt   1560
cgccctggac ccgcccaacg atttgtcgtc actgtcaagg tttgacctgc acttcatttg   1620
gggcccacat acaccaaaaa aatgctgcat aattctcggg gcagcaagtc ggttacccgg   1680
ccgccgtgct ggaccgggtt gaatggtgcc cgtaactttc ggtagagcgg acggccaata   1740
ctcaacttca aggaatctca cccatgcgcg ccggcgggga accggagttc ccttcagtga   1800
gcgttattag ttcgccgctc ggtgtgtcgt agatactagc ccctggggca cttttgaaat   1860
ttgaataaga tttatgtaat cagtctttta ggtttgaccg gttctgccgc tttttttaaa   1920
attggatttg taataataaa acgcaattgt ttgttattgt ggcgctctat catagatgtc   1980
gctataaacc tattcagcac aatatattgt tttcatttta atattgtaca tataagtagt   2040
agggtacaat cagtaaattg aacggagaat attattcata aaaatacgat agtaacgggt   2100
gatatattca ttagaatgaa ccgaaaccgg cggtaaggat ctgagctaca catgctcagg   2160
ttttttacaa cgtgcacaac agaattgaaa gcaaatatca tgcgatcata ggcgtctcgc   2220
atatctcatt aaagcaggac tctagtcgag atgccgagaa cgacctctac accacatccc   2280
ttcgattccg attactccga gagcatggat tcaatgtttc atgcgacgta ttcaacaagt   2340
ttaaagacga gcaagggaat ttcaagtcat ccgtgacaag cgatgttcga ggattgttgg   2400
aactttacca agcttcctat ttgagggttc atggggaaga tatattggat gaagcaattt   2460
ctttcaccac caaccattta agccttgcag tagcatcttt ggactatccg ttatccgaag   2520
aggtttcaca tgctttgaaa caatcaattc gaagaggctt gccaagggtt gaggcaagac   2580
actatctttc agtataccaa gatattgagt cccataataa ggttttgttg gagtttgcta   2640
agatcgattt caacatggta caacttttgc ataggaaaga gctaagtgag atttctaggt   2700
ggtggaagga tttagacttt caaagaaagt tgccatacgc aagagataga gtggttgaag   2760
gctatttttg gatctcagga gtgtactttg agccccaata ttctcttggt agaaagatgt   2820
tgacaaaagt gatagccatg gcttctattg tggaggatcc aagcttatcg atttcgaacc   2880
cagcttccca actgtaatca atccaaatgt aagatcaatg ataacacaat gacatgatct   2940
atcatgttac cttgtttatt catgttcgac taattcattt aattaatagt caatccattt   3000
agaagttaat aaaactacaa gtattattta gaaattaata agaatgttga ttgaaaaata   3060
atactatata aaattgatag atcttgcgct ttgttatatt agcattagat tatgttttgt   3120
tacattagat tactgtttct attagtttga tattatttgt tactttagct tgttatttaa   3180
tattttgttt attgataaat tacaagcaga ttggaatttc taacaaaata tttattaact   3240
```

-continued

```
tttaaactaa aatatttagt aatggtatag atatttaatt atataataaa ctattaatca   3300

taaaaaaata ttattttaat ttatttattc ttatttttac tatagtattt tatcattgat   3360

atttaattca tcaaaccagc tagaattact attatgatta aacaaatat taatgctagt   3420

atatcatctt acatgttcga tcaaattcat taaaaataat atacttactc tcaactttta   3480

tcttcttcgt cttacacatc acttgtcata ttttttaca ttactatgtt gtttatgtaa   3540

acaatatatt tataaattat tttttcacaa ttataacaac tatattatta taatcatact   3600

aattaacatc acttaactat tttatactaa aaggaaaaaa gaaaataatt atttccttac   3660

caagctgggg taccgaattc ggatcctcca caatagaagc catggctatc acttttgtca   3720

acatctttct accaagagaa tattggggct caaagtacac tcctgagatc caaaaatagc   3780

cttcaaccac tctatctctt gcgtatggca actttctttg aaagtctaaa tccttccacc   3840

acctagaaat ctcacttagc tctttcctat gcaaaagttg taccatgttg aaatcgatct   3900

tagcaaactc caacaaaacc ttattatggg actcaatatc ttggtatact gaaagatagt   3960

gtcttgcctc aacccttggc aagcctcttc gaattgattg tttcaaagca tgtgaaacct   4020

cttcggataa cggatagtcc aaagatgcta ctgcaaggct taaatggttg gtggtgaaag   4080

aaattgcttc atccaatata tcttccccat gaaccctcaa ataggaagct tggtaaagtt   4140

ccaacaatcc tcgaacatcg cttgtcacgg atgacttgaa attcccttgc tcgtctttaa   4200

acttgttgaa tacgtcgcat gaaacattga atccatgctc tcggagtaat cggaatcgaa   4260

gggatgtggt gtagaggtcg ttctcggcat ctcgagcggc cgccagtgtg atggatatct   4320

gcagaattcg gcttgggacg cgtatcgatt acgataagct ctgtattttg ttactgtgtg   4380

atggtaatag caaagagtgg taatgtattt atagaaggtg gagctgtgga aggtgatatt   4440

tttgcatgca aatcttcatc aacgtgttga agacattgac atgcaagatg acgagtgtgc   4500

aaattaaaga agacgaaata ttgtctcttt tttttttttt ttgtatagtg gtgggtagat   4560

atcgagatgc cacatccctt cacatggtac tagcaaggtt cggacaaact ttgttgcagg   4620

ggggttcatg gttgcatctg taactggaag gggcgaaatg atgatgcttt aacagcagaa   4680

agatgatgga ccgtgttgtg ttgtatgtga actcagttga attcaaagag tgttgaaact   4740

gggaagggtt ttaaagtgag acagagatgt cccgattcac tgagttaagg gttgagttga   4800

tagaggacaa gtcaagtgta cacatgttgc tgtgcatggt gatgatctat gagttgcagg   4860

agatatgaac aaattcagat atgtatactt ttggtatcct gtacgtttga tgctcataca   4920

aattagtcct ttcaaagttt gaggtatttt tattcttttt caataaatatt atctaagtat   4980

tacatattat atcattatat aaatttatat aataagaatg gaaaataaaa tgtttcacta   5040

aaaacgctta aaagtaagga tttggattca atatagataa tagtatataa gttatacagt   5100

ccaatctaac ataaggtgcc acgtattaag aaatatggta atttattttt tcataaattt   5160

taaattaatt atactattta ttaataattt tatataatcc taacaatata ttatactatg   5220

ttagtttatt aaaaacaaac aagtaggcga ggggctaggg ccatgactct ttaattttag   5280

ggtaatctat aaaaatagtc atttttgttt gcctcaggtt atattttaat catttatgtt   5340

tgaaatgtta cactttagtc acttttgtta ttattttgtt acaaagtgat cactctaccg   5400

ttaagctccg ttatctctct aacgataatc ctacatggca gtccaactaa attttaggtg   5460

tcaacttgga tttctaaata ggatgaaaat agctgcaggc atgcaagctt aagccgaatt   5520

ccagcacact ggcggccgtt actagtgata tcccgcggcc atggcggccg ggagcatgcg   5580

acgtcgggcc caattcgccc tatagtgagt cgtattacaa ttcactggcc gtcgttttac   5640
```

```
aacgtcgtga ctgggaaaac cctggcgtta cccaacttaa tcgccttgca gcacatcccc   5700
ctttcgccag ctggcgtaat agcgaagagg cccgcaccga tcgcccttcc caacagttgc   5760
gcagcctgaa tggcgaatgg aaattgtaag cgttaatggg tttctggagt ttaatgagct   5820
aagcacatac gtcagaaacc attattgcgc gttcaaaagt cgcctaaggt cactatcagc   5880
tagcaaatat ttcttgtcaa aaatgctcca ctgacgttcc ataaattccc ctcggtatcc   5940
aattagagtc tcatattcac tctcaatcca aataatctgc aatggcaatt accttatccg   6000
caacttcttt acctatttcc gcccggatcc gggcaggttc tccggccgct tgggtggaga   6060
ggctattcgg ctatgactgg gcacaacaga caatcggctg ctctgatgcc gccgtgttcc   6120
ggctgtcagc gcaggggcgc ccggttcttt ttgtcaagac cgacctgtcc ggtgccctga   6180
atgaactgca ggacgaggca gcgcggctat cgtggctggc cacgacgggc gttccttgcg   6240
cagctgtgct cgacgttgtc actgaagcgg gaagggactg gctgctattg ggcgaagtgc   6300
cggggcagga tctcctgtca tctcaccttg ctcctgccga gaaagtatcc atcatggctg   6360
atgcaatgcg gcggctgcat acgcttgatc cggctacctg cccattcgac caccaagcga   6420
aacatcgcat cgagcgagca cgtactcgga tggaagccgg tcttgtcgat caggatgatc   6480
tggacgaaga gcatcagggg ctcgcgccag ccgaactgtt cgccaggctc aaggcgcgca   6540
tgcccgacgg cgaggatctc gtcgtgaccc atggcgatgc ctgcttgccg aatatcatgg   6600
tggaaaatgg ccgcttttct ggattcatcg actgtggccg gctgggtgtg gcggaccgct   6660
atcaggacat agcgttggct acccgtgata ttgctgaaga gcttggcggc gaatgggctg   6720
accgcttcct cgtgctttac ggtatcgccg ctcccgattc gcagcgcatc gccttctatc   6780
gccttcttga cgagttcttc tgagcgggac tctggggttc gaaatgaccg accaagcgac   6840
gcccaacctg ccatcacgag atttcgattc caccgccgcc ttctatgaaa ggttgggctt   6900
cggaatcgtt ttccgggacg ccggctggat gatcctccag cgcggggatc tcatgctgga   6960
gttcttcgcc caccccgatc caacacttac gtttgcaacg tccaagagca aatagaccac   7020
gaacgccgga aggttgccgc agcgtgtgga ttgcgtctca attctctctt gcaggaatgc   7080
aatgatgaat atgatactga ctatgaaact ttgagggaat actgcctagc accgtcacct   7140
cataacgtgc atcatgcatg ccctgacaac atggaacatc gctatttttc tgaagaatta   7200
tgctcgttgg aggatgtcgc ggcaattgca gctattgcca aaatcgaaat acccctcacg   7260
catgcattca tcaatattat tcatgcgggg aaaggcaaga ttaatccaac tggcaaatca   7320
tccagcgtga ttggtaactt cagttccagc gacttgattc gttttggtgc tacccacgtt   7380
ttcaataagg acgagatggt ggagtaaaga aggagtgcgt cgaagcagat cgttcaaaca   7440
tttggcaata aagtttctta agattgaatc ctgttgccgg tcttgcgatg attatcatat   7500
aatttctgtt gaattacgtt aagcatgtaa taattaacat gtaatgcatg acgttattta   7560
tgagatgggt ttttatgatt agagtcccgc aattatacat ttaatacgcg atagaaaaca   7620
aaatatagcg cgcaaactag gataaattat cgcgcgcggt gtcatctatg ttactagatc   7680
gaattaattc agtacattaa aaacgtccgc aatgtgttat taagttgtct aagcgtcaat   7740
ttgtttacat tttggattct tgcagtcacg ttaatataat ttcttggaac tacatttttt   7800
ccaaaaccta tttgctcaat ttggtaacaa agaagcctcc ttgtactaat aataaaaata   7860
aaaaaaggct agctttctgg tattgcttaa acatgaaatg tctaacccat agagcacttg   7920
atagatgctt agtacatcaa actttctttt cggaagaaag taccatggca ctaagttact   7980
```

-continued

```
gcgacacttc attttcttg aagaacccct tttcaacttc tatgtccagc ccataggtat   8040
aacctccata gacccacatg atatgatata tggaaaaact tagaaaagct tgaatatacc   8100
catgtcaaaa cctgagtcct agtaacaaag ccttggtata taagatcatc aatgaaacaa   8160
catttggttt tgattcccaa gatatgaact tttaatctaa aatcgtacga gtattagttt   8220
gcttgcaacg tataaactat ggttttattt tgcaatttga gagcagaaca agacatggat   8280
ttctattccc aaggaaattt tagttgaacc ttctttcttt ttaattttat ttgctaaatt   8340
ttttggtgtt atacagggga tggatgataa agtagtccca ccttcaatga ctgatttcgt   8400
tcatagggtt ctgccaagtg ctgcagttca taaactccca tatgagggtc attttacata   8460
tttatatttc tgtgatgaat gccatagaca gatatttacc acactttttg gaaccccaca   8520
aggccctctc cctgtcaaca ataccataga agtggaacaa acaccattgg atgatataca   8580
agtgcaggaa gatgcttcaa ctcaggatga ttttaagaca gactgagata tcgaagtttt   8640
ctacaattag gtttgagttt tgacatgtaa tgtaaggttg gttgtatata tagcataggt   8700
ttattctatc acttgtgatt agaaaagttg aataaaattt tctcatatat ttatgtggca   8760
atggaatgga gatttgagaa acattttgaa gttgttggct ggctacaatg gaaataaaca   8820
taatcaagga aaaggtgatg acttgttctg atttgttgtt agctgctttc aatttaatct   8880
tgagacaata gttttttac a                                              8901
```

<210> SEQ ID NO 5
<211> LENGTH: 2231
<212> TYPE: DNA
<213> ORGANISM: Gossypium hirsutum

<400> SEQUENCE: 5

```
gtgcagctat gtttgctcca atggtcaatc cttatgattc actgatgaat aggggagaaa     60
gatatggaat ctgggaaaag tggactcgga aaaggaaatt tatgtatttt ttggctcgaa    120
gatttcctaa atttctatct tacttctacc ggcaaagctt cctctctgga aagcatggtc    180
agattgatca atggctagca ttgacactgg gaagaagggt gagtgatttt ctacactatg    240
agctctctaa ggttccggaa tccagttaag tacagtgcat aatatgcaat tttttgtttc    300
caaggcactc tacggtctta aatgtggaaa tgcataatat tctaagcgag ttactagatt    360
tttgcagcat ttcacttgtc aagcatcgaa tctaaattca tatattgtct ttacaggata    420
gagctttgat agaagaccct atctatgaag aattctggca aagggatgtc gaagaatcaa    480
tccgacaagg aaatgcaaaa ccttttgtgg aggaagctgt attgcaagtt tctaattggg    540
gattcagcct tgcagacctc aaattacaga agaaacagag aggaaaagga atcctaaatt    600
tgatcaagtt ttttcttagt ggctctgagg aagaatatac tggttttctt ggtccaatac    660
acatatggca ggtataattt catcctatgt tgctgtgact cttccatttt cttgaactac    720
tcgtatcttt cacttgtgtc caacacatat ctagacatat gatccttcaa agaccctcca    780
attacatgga aaaacttgtt aaagaaaaag aacataccta tgttggaatg gacctgtatc    840
tggtactcaa actcacctga gtaacataga ttccatcctt attcatacat tgccgctgca    900
ttaaactgtt ctgctacact ttttcctgtt cattgaagca ttacggattt actgatctat    960
tgttttctag tgtaatatgt gatagctgag aagttctttg ctttagaggc ttccatttta   1020
cttttgtttt tgtggttaat ttgttgccaa ctattatcat atttaacttg ctttttacat   1080
tttggattct tgcagtcacg ttaatataat ttcttggaac tacatttttt ccaaaaccta   1140
tttgctcaat ttggtaacaa agaagcctcc ttgtactaat aataaaaata aaaaaaggct   1200
```

```
agctttctgg tattgcttaa acatgaaatg tctaacccat agagcacttg atagatgctt   1260

agtacatcaa actttctttt cggaagaaag taccatggca ctaagttact gcgacacttc   1320

atttttcttg aagaacccct tttcaacttc tatgtccagc ccataggtat aacctccata   1380

gacccacatg atatgatata tggaaaaact tagaaaagct tgaatatacc catgtcaaaa   1440

cctgagtcct agtaacaaag ccttggtata taagatcatc aatgaaacaa catttggttt   1500

tgattcccaa gatatgaact tttaatctaa aatcgtacga gtattagttt gcttgcaacg   1560

tataaactat ggttttattt tgcaatttga gagcagaaca agacatggat ttctattccc   1620

aaggaaattt tagttgaacc ttctttcttt ttaattttat ttgctaaatt ttttggtgtt   1680

atacagggga tggatgataa agtagtccca ccttcaatga ctgatttcgt tcatagggtt   1740

ctgccaagtg ctgcagttca taaactccca tatgagggtc attttacata tttatatttc   1800

tgtgatgaat gccatagaca gatatttacc acactttttg gaaccccaca aggccctctc   1860

cctgtcaaca ataccataga agtggaacaa acaccattgg atgatataca agtgcaggaa   1920

gatgcttcaa ctcaggatga ttttaagaca gactgagata tcgaagtttt ctacaattag   1980

gtttgagttt tgacatgtaa tgtaaggttg gttgtatata tagcataggt ttattctatc   2040

acttgtgatt agaaaagttg aataaaattt tctcatatat ttatgtggca atggaatgga   2100

gatttgagaa acattttgaa gttgttggct ggctacaatg gaaataaaca taatcaagga   2160

aaaggtgatg acttgttctg atttgttgtt agctgctttc aatttaatct tgagacaata   2220

gttttttac a                                                         2231
```

```
<210> SEQ ID NO 6
<211> LENGTH: 25
<212> TYPE: DNA
<213> ORGANISM: Artificial sequence
<220> FEATURE:
<223> OTHER INFORMATION: Primer

<400> SEQUENCE: 6

ggaatggacc tgtatctggt actca                                           25
```

```
<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7

tttgcgacaa catgtcgagg c                                               21
```

```
<210> SEQ ID NO 8
<211> LENGTH: 912
<212> TYPE: DNA
<213> ORGANISM: Artificial sequence
<220> FEATURE:
<223> OTHER INFORMATION: Probe

<400> SEQUENCE: 8

gccgttacta gtgatatccc gcggccatgg cggccgggag catgcgacgt cgggcccaat     60

tcgccctata gtgagtcgta ttacaattca ctggccgtcg ttttacaacg tcgtgactgg    120

gaaaaccctg gcgttaccca acttaatcgc cttgcagcac atcccccttt cgccagctgg    180

cgtaatagcg aagaggcccg caccgatcgc ccttcccaac agttgcgcag cctgaatggc    240
```

```
gaatggaaat tgtaagcgtt aatgggtttc tggagtttaa tgagctaagc acatacgtca    300

gaaaccatta ttgcgcgttc aaaagtcgcc taaggtcact atcagctagc aaatatttct    360

tgtcaaaaat gctccactga cgttccataa attcccctcg gtatccaatt agagtctcat    420

attcactctc aatccaaata atctgcaatg gcaattacct tatccgcaac ttctttacct    480

atttccgccc ggatccgggc aggttctccg gccgcttggg tggagaggct attcggctat    540

gactgggcac aacagacaat cggctgctct gatgccgccg tgttccggct gtcagcgcag    600

gggcgcccgg ttctttttgt caagaccgac ctgtccggtg ccctgaatga actgcaggac    660

gaggcagcgc ggctatcgtg gctggccacg acgggcgttc cttgcgcagc tgtgctcgac    720

gttgtcactg aagcgggaag ggactggctg ctattgggcg aagtgccggg gcaggatctc    780

ctgtcatctc accttgctcc tgccgagaaa gtatccatca tggctgatgc aatgcggcgg    840

ctgcatacgc ttgatccggc tacctgccca ttcgaccacc aagcgaaaca tcgcatcgag    900

cgagcacgta ct                                                        912
```

<210> SEQ ID NO 9
<211> LENGTH: 708
<212> TYPE: DNA
<213> ORGANISM: Artificial sequence
<220> FEATURE:
<223> OTHER INFORMATION: Probe

<400> SEQUENCE: 9

```
ctgctgagcc tcgacatgtt gtcgcaaaat tcgccctgga cccgcccaac gatttgtcgt     60

cactgtcaag gtttgacctg cacttcattt ggggcccaca tacaccaaaa aaatgctgca    120

taattctcgg ggcagcaagt cggttacccg gccgccgtgc tggaccgggt tgaatggtgc    180

ccgtaacttt cggtagagcg gacggccaat actcaacttc aaggaatctc acccatgcgc    240

gccggcgggg aaccggagtt cccttcagtg agcgttatta gttcgccgct cggtgtgtcg    300

tagatactag cccctggggc acttttgaaa tttgaataag atttatgtaa tcagtctttt    360

aggtttgacc ggttctgccg cttttttttaa aattggattt gtaataataa aacgcaattg    420

tttgttattg tggcgctcta tcatagatgt cgctataaac ctattcagca caatatattg    480

ttttcatttt aatattgtac atataagtag tagggtacaa tcagtaaatt gaacggagaa    540

tattattcat aaaaatacga tagtaacggg tgatatattc attagaatga accgaaaccg    600

gcggtaagga tctgagctac acatgctcag gttttttaca acgtgcacaa cagaattgaa    660

agcaaatatc atgcgatcat aggcgtctcg catatctcat taaagcag                 708
```

<210> SEQ ID NO 10
<211> LENGTH: 581
<212> TYPE: DNA
<213> ORGANISM: Artificial sequence
<220> FEATURE:
<223> OTHER INFORMATION: Probe

<400> SEQUENCE: 10

```
acatcccttc gattccgatt actccgagag catggattca atgtttcatg cgacgtattc     60

aacaagttta aagacgagca agggaatttc aagtcatccg tgacaagcga tgttcgagga    120

ttgttggaac tttaccaagc ttcctatttg agggttcatg ggaagatat attggatgaa     180

gcaatttctt tcaccaccaa ccatttaagc cttgcagtag catctttgga ctatccgtta    240

tccgaagagg tttcacatgc tttgaaacaa tcaattcgaa gaggcttgcc aagggttgag    300

gcaagacact atctttcagt ataccaagat attgagtccc ataataaggt tttgttggag    360
```

```
tttgctaaga tcgatttcaa catggtacaa cttttgcata ggaaagagct aagtgagatt    420

tctaggtggt ggaaggattt agactttcaa agaaagttgc catacgcaag agatagagtg    480

gttgaaggct atttttggat ctcaggagtg tactttgagc cccaatattc tcttggtaga    540

aagatgttga caaaagtgat agccatggct tctattgtgg a                        581


<210> SEQ ID NO 11
<211> LENGTH: 575
<212> TYPE: DNA
<213> ORGANISM: Artificial sequence
<220> FEATURE:
<223> OTHER INFORMATION: Probe

<400> SEQUENCE: 11

tattcatgtt cgactaattc atttaattaa tagtcaatcc atttagaagt taataaaact     60

acaagtatta tttagaaatt aataagaatg ttgattgaaa aataatacta tataaaattg    120

atagatcttg cgctttgtta tattagcatt agattatgtt ttgttacatt agattactgt    180

ttctattagt ttgatattat ttgttacttt agcttgttat ttaatatttt gtttattgat    240

aaattacaag cagattggaa tttctaacaa aatatttatt aacttttaaa ctaaaatatt    300

tagtaatggt atagatattt aattatataa taaactatta atcataaaaa aatattattt    360

taatttattt attcttattt ttactatagt attttatcat tgatatttaa ttcatcaaac    420

cagctagaat tactattatg attaaaacaa atattaatgc tagtatatca tcttacatgt    480

tcgatcaaat tcattaaaaa taatatactt actctcaact tttatcttct tcgtcttaca    540

catcacttgt catatttttt tacattacta tgttg                              575


<210> SEQ ID NO 12
<211> LENGTH: 1140
<212> TYPE: DNA
<213> ORGANISM: Artificial sequence
<220> FEATURE:
<223> OTHER INFORMATION: Probe

<400> SEQUENCE: 12

gattacgata agctctgtat tttgttactg tgtgatggta atagcaaaga gtggtaatgt     60

atttatagaa ggtggagctg tggaaggtga tatttttgca tgcaaatctt catcaacgtg    120

ttgaagacat tgacatgcaa gatgacgagt gtgcaaatta aagaagacga aatattgtct    180

cttttttttt ttttttgtat agtggtgggt agatatcgag atgccacatc ccttcacatg    240

gtactagcaa ggttcggaca aactttgttg caggggggtt catggttgca tctgtaactg    300

gaaggggcga aatgatgatg ctttaacagc agaaagatga tggaccgtgt tgtgttgtat    360

gtgaactcag ttgaattcaa agagtgttga aactgggaag ggttttaaag tgagacagag    420

atgtcccgat tcactgagtt aagggttgag ttgatagagg acaagtcaag tgtacacatg    480

ttgctgtgca tggtgatgat ctatgagttg caggagatat gaacaaattc agatatgtat    540

acttttggta tcctgtacgt ttgatgctca tacaaattag tcctttcaaa gtttgaggta    600

tttttattct ttttcaataa tattatctaa gtattacata ttatatcatt atataaattt    660

atataataag aatggaaaat aaaatgtttc actaaaaacg cttaaaagta aggatttgga    720

ttcaatatag ataatagtat ataagttata cagtccaatc taacataagg tgccacgtat    780

taagaaatat ggtaatttat tttttcataa attttaaatt aattatacta tttattaata    840

attttatata atcctaacaa tatattatac tatgttagtt tattaaaaac aaacaagtag    900
```

-continued

```
gcgaggggct agggccatga ctctttaatt ttagggtaat ctataaaaat agtcattttt    960

gtttgcctca ggttatattt taatcattta tgtttgaaat gttacacttt agtcactttt   1020

gttattattt tgttacaaag tgatcactct accgttaagc tccgttatct ctctaacgat   1080

aatcctacat ggcagtccaa ctaaatttta ggtgtcaact tggatttcta aataggatga   1140
```

COTTON TRANSGENIC EVENT TAM66274

CROSS-REFERENCE TO RELATED APPLICATIONS

This application claims the benefit of U.S. Provisional Application No. 62/530,740, filed Jul. 10, 2017, herein incorporated by reference in its entirety.

INCORPORATION OF SEQUENCE LISTING

The sequence listing contained in the file named "TAMC055US_ST25.txt", which is 31.3 kilobytes (size as measured in Microsoft Windows®) and was created on Jul. 9, 2018, is filed herewith by electronic submission and is incorporated by reference herein.

FIELD OF THE INVENTION

The invention relates to transgenic *Gossypium hirsutum* event TAM66274. The event exhibits an ultra-low gossypol cotton seed ("ULGCS") trait. The invention also relates to plants, plant parts, plant seeds, plant cells, agricultural products, and methods related to event TAM66274 and provides nucleotide molecules that are unique to the event and were created in connection with the insertion of transgenic DNA into the genome of a *Gossypium hirsutum* plant.

BACKGROUND OF THE INVENTION

Cotton (*Gossypium hirsutum*) is an important crop in many areas of the world, and the methods of biotechnology have been applied to this crop in order to produce cotton with desirable traits. One such desirable trait is ultra-low gossypol levels in cotton seeds. The expression of a ultra-low gossypol level transgene in a plant can confer the desirable trait of ultra-low gossypol levels in cotton seeds in the plant, but expression of the transgene may be influenced by the chromosomal location and the genomic result of the transgene insertion. For example, it has been observed in plants that there often is variation in the level and pattern of transgene expression among individual events that differ in the chromosomal insertion site of the transgene but are otherwise identical. There may also be undesirable and/or desirable phenotypic or agronomic differences between events. Because of this, it is often necessary to produce and analyze a large number of individual plant transformation events in order to select an event having both the desirable trait and the optimal phenotypic and agricultural characteristics necessary to make it suitable for commercial purposes. Such selection often requires greenhouse and field trials with many events over multiple years, in multiple locations, and under a variety of conditions so that a significant amount of agronomic, phenotypic, and molecular data may be collected. The resulting data and observations must then be analyzed by teams of scientists and agronomists with the goal of selecting a commercially suitable event. Such an event, once selected, may then be used for introgressing the desirable trait into other genetic backgrounds using plant breeding methods, and thus producing a number of different crop varieties that contain the desirable trait and are suitably adapted to specific local growing conditions.

SUMMARY OF THE INVENTION

The invention provides transgenic cotton plants comprising event TAM66274, which exhibit ultra-low gossypol levels in cotton seeds, having a representative seed sample deposited with the American Type Culture Collection (ATCC®) under Patent Deposit Designation PTA-124218. The invention also provides novel DNA molecules related to cotton event TAM66274 and methods of using these molecules. The invention also provides seeds, progeny, plant parts, cells, and commodity products of cotton plants comprising event TAM66274. The invention also provides methods of using cotton event TAM66274 and methods of producing cotton with ultra-low gossypol levels in cotton seeds.

The invention provides recombinant DNA molecules related to cotton event TAM66274. These recombinant DNA molecules may comprise nucleotide molecules having a nucleotide sequence representing a region of the genomic DNA flanking the transgene insertion, and/or a region of the transgene insertion, and/or a contiguous sequence of any of these regions such as a region of the junction between the transgene insertion and flanking genomic DNA of cotton event TAM66274. The invention also provides DNA molecules useful as primers and probes diagnostic for cotton event TAM66274 and amplicons diagnostic for the presence of cotton event TAM66274. Cotton plants, plant cells, plant parts, commodity products, progeny, and seeds comprising these molecules are also disclosed.

The invention provides methods, compositions, and kits useful for detecting the presence and/or absence of DNA derived from cotton event TAM66274 and thus the presence and/or absence of the event. The invention provides a method for detection of TAM66274 by contacting a sample comprising DNA with a primer set that when used in a nucleic acid amplification reaction with genomic DNA from a cotton plant or seed comprising event TAM66274 produces an amplified DNA diagnostic for cotton event TAM66274, performing a nucleic acid amplification reaction thereby producing the amplified DNA, and detecting the presence and/or absence of the amplified DNA. The invention also provides a method for detection of event TAM66274 by contacting a sample comprising DNA with a probe that when used in a hybridization reaction with DNA from cotton event TAM66274 hybridizes to a DNA molecule specific for cotton event TAM66274, performing a hybridization reaction, and detecting the hybridization of the probe to the DNA molecule. Kits comprising the methods and compositions of the invention useful for detecting the presence of DNA derived from cotton event TAM66274 are also provided.

The invention provides a cotton plant, seed, plant cell, progeny plant, plant part, or commodity product derived from a plant, plant cell, or seed comprising cotton event TAM66274. The invention also provides a cotton plant, seed, plant cell, progeny plant, plant part, or commodity product comprising a recombinant DNA molecule having a nucleotide sequence selected from the group consisting of SEQ ID NO:1-4, and complements and fragments thereof. The invention also provides a cotton plant, seed, plant cell, progeny plant, plant part, or commodity product derived from the plant or seed comprising cotton event TAM66274 and comprising a recombinant DNA molecule that produces an amplified DNA molecule comprising a sequence selected from SEQ ID NO:1-4 in a DNA amplification method.

The invention provides methods of producing a cotton plant and/or seed that has ultra-low gossypol levels in cotton seeds by sexually crossing a cotton event TAM66274 containing plant comprising a sequence selected from SEQ ID NO:1-4 with a second cotton plant, thereby producing seed, growing the seed to produce progeny plants, and selecting a progeny plant that exhibits ultra-low gossypol levels in cotton seeds. The methods may also include selfing the selected progeny plant to produce a plurality of second generation progeny plants and selecting from these a plant with ultra-low gossypol level in the seed. The methods may also include sexually crossing the selected progeny plant with another cotton plant to produce seed, growing the seed to produce a second generation of progeny plants, and selecting a second generation progeny plant that exhibits ultra-low gossypol levels in cotton seeds. The invention provides methods of producing a cotton plant and/or seed that exhibits ultra-low gossypol levels in cotton seeds by selfing a ultra-low gossypol level cotton plant comprising event TAM66274 comprising a sequence selected from SEQ ID NO:1-4, thereby producing seed, growing the seed to produce progeny plants, and selecting a progeny plant that exhibits ultra-low gossypol level. The invention also provides a cotton plant having ultra-low gossypol seed values and methods of using the same. The foregoing and other aspects of the invention will become more apparent from the following detailed description.

BRIEF DESCRIPTION OF THE SEQUENCES

SEQ ID NO:1 is a sequence representing the RB 5' transgene insertion junction containing 200 bp of flanking genomic and 200 bp of T-DNA insert.

SEQ ID NO:2 is a sequence representing the LB 3' transgene insertion junction containing 200 bp of flanking genomic and 200 bp of T-DNA insert.

SEQ ID NO:3 is a full contig sequence comprising 200 bp of the 5' genomic sequence flanking the insertion, the T-DNA insert sequence, and the 200 bp of the 3' genomic sequence flanking the insertion. SEQ ID NO:3 comprises SEQ ID NOs:1 and 2.

SEQ ID NO:4 is a full contig sequence comprising 1035 bp of the 5' genomic sequence flanking the insertion, 6714 bp sequence of the T-DNA insert, and 1152 bp of the 3' genomic sequence flanking the insertion. SEQ ID NO:4 comprises SEQ ID NO:3, which comprises SEQ ID NOs:1, 2, and 3.

SEQ ID NO:5 is the native genomic sequence at the site of the T-DNA insertion in event TAM66274.

SEQ ID NO:6 is the 274 flank-RB-691F primer.

SEQ ID NO:7 is the OCS-581R primer.

SEQ ID NO:8 is Probe 1.

SEQ ID NO:9 is Probe 13.

SEQ ID NO:10 is Probe 14.

SEQ ID NO:11 is Probe 15.

SEQ ID NO:12 is Probe 16.

DETAILED DESCRIPTION

The following definitions and methods are provided to better define the invention and to guide those of ordinary skill in the art in the practice of the invention. Unless otherwise noted, terms are to be understood according to conventional usage by those of ordinary skill in the relevant art.

Figure 9:
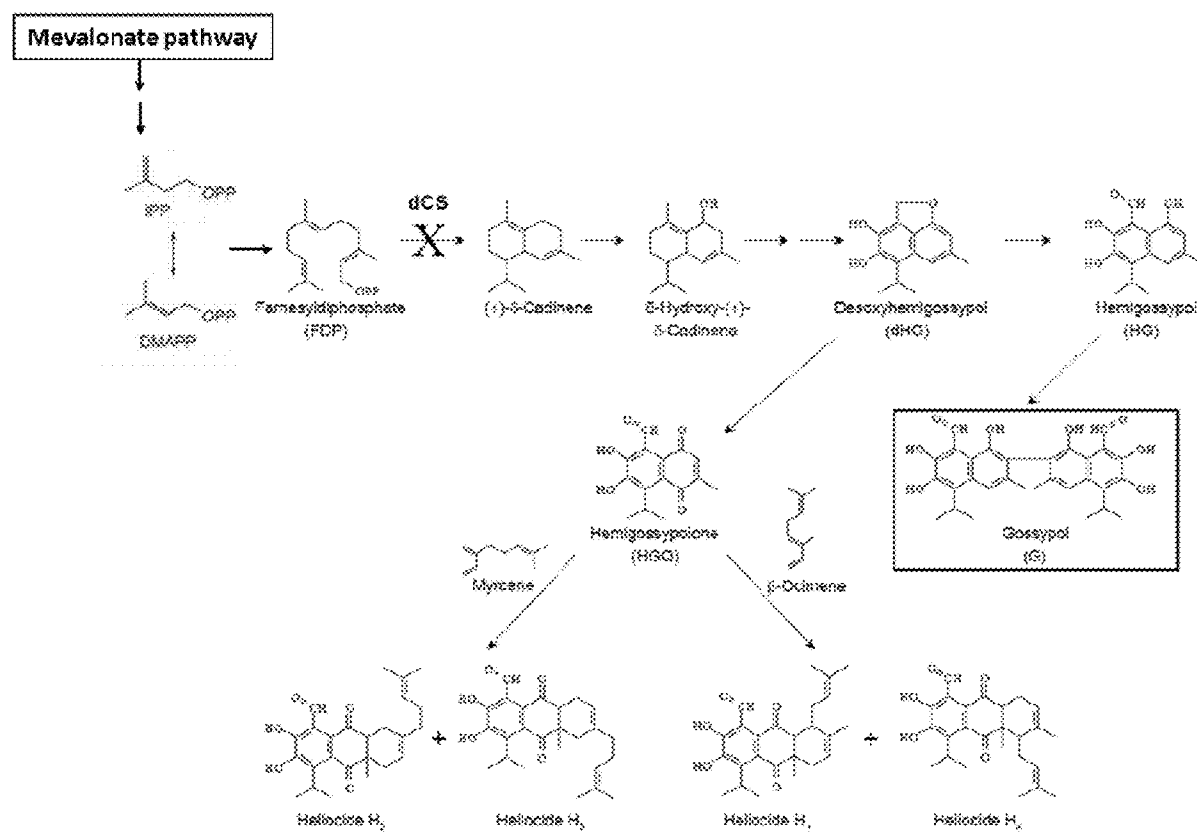
FIG. 9 is a schematic of the mevalonate pathway whereby dCS catalyzes the first committed step involving the cyclization of Farnesyl diphosphate (FDP) to (+)-δ-cadinene. Gossypol is the predominant terpenoid present in the glands of the seed kernel and flower petals, whereas the glands in other parts of the plant contain gossypol and additional protective terpenoids derived from the same biosynthetic pathway. Gossypol is the predominant terpenoid found in the cotton seed, with only traces of desoxyhemigossypol (dHG) and hemigossypol.

Gossypol is a terpenoid produced in dark colored, pigment glands of plants belonging to the genus *Gossypium* of the family Malvaceae. Gossypol and related terpenoids are present throughout the cotton plant in the glands of foliage, floral organs, bolls, roots and seeds. Constitutive presence of these compounds protects the plant from both insects and pathogens. The compounds are induced in response to microbial infections as well as insect herbivory. Many of these terpenoids are also induced in response to fungal or bacterial infection and serve as phytoalexins. These terpenoids are derived from (+)-δ-cadinene. As shown in FIG. 9, dCS catalyzes the first committed step involving the cyclization of FDP to (+)-δ-cadinene. Gossypol is the predominant terpenoid present in the glands of the seed kernel and flower petals, whereas the glands in other parts of the plant contain gossypol and additional protective terpenoids derived from the same biosynthetic pathway. Gossypol is the predominant terpenoid found in the cotton seed, with only traces of desoxyhemigossypol (dHG) and hemigossypol.

Although cotton seed is a rich source of relatively high quality protein and is used as a feed supplement for ruminant animals, due to the presence of toxic gossypol, it is not typically consumed by humans or other monogastric animals, such as pigs, birds, fish, and rodents, which are more sensitive to gossypol toxicity than ruminants. Gossypol causes heart and liver damage in monogastric animals, including humans. Gossypol poisoning has been reported in several species, including pigs, broiler chicks, dogs, sheep, and goats. Adult ruminant animals are able to tolerate a limited amount of gossypol in their diets because gossypol is bound during ruminal fermentation and becomes unavailable for intestinal absorption. Therefore, cotton seed is currently used mainly as feed for ruminant animals as either whole seed or cotton seed meal after oil extraction. As a secondary product of one of the most widely cultivated fiber crops globally, cotton seed is a readily available source of high quality protein that could be used in human food and feed for monogastric animals if not for the presence of gossypol. Grown by 20 million farmers in 80 different countries, enough cotton seed is produced globally to meet the daily protein requirements of a half a billion people per year. Rising incomes and diversifying diets in developing countries will increase demand for feed in livestock and aquaculture production.

Historically, limitations on the use of cotton seed due to the presence of gossypol have led to efforts to reduce gossypol through processing and breeding. Production of high quality protein products from conventional cotton seed, but low in free gossypol, has been demonstrated using several processes: air classification, liquid cyclone processing, solvent extraction, and screw-press techniques. While all of these processes resulted in cotton seed protein products with free gossypol levels below limits established by FDA, the processing steps were cost prohibitive. For example, the liquid cyclone process was capable of producing edible cotton seed for food uses that contained 400 ppm or less free gossypol and more than 65% protein.

A gossypol-free mutant "glandless" cotton strain, which lacked the glands where gossypol and other terpenoids are stored, was identified in the 1950s and was used to breed the trait into commercial varieties. This generated a great deal of excitement and provided hope for the utilization of glandless cotton seed as feed for monogastric animals and for human food. Unfortunately, due to the lack of the glands and, therefore, the lack of the protective terpenoids in the vegetative and floral parts of the plant, glandless cotton varieties suffered more severe pest damage from traditional and also non-traditional cotton pests and also had lower yields under field conditions. Thus, although the glandless cotton seed proved fit as a source of food and feed, it was not widely accepted by cotton growers. The glandless cotton experience underscored the importance of maintaining the protective terpenoids in the vegetative and floral parts of the plant.

To address these significant shortcomings, the present invention provides, in one embodiment, a transgenic cotton event TAM66274 that exhibits ultra-low gossypol levels only in the seeds while maintaining normal levels of gossypol and related terpenoids in rest of the plant. The event comprises a single insertion of transgenic DNA in the cotton genome. An "event" is produced by: (i) transformation of a plant cell with a nucleic acid construct that includes a transgene of interest, (ii) regeneration of a population of plants resulting from the insertion of the transgene into the genome of the plant, and (iii) selection of a particular plant characterized by insertion of the transgene into a particular location in the plant's genome.

The term "event" refers to a new transgenic genomic molecular structure comprising the inserted DNA and the flanking cotton genomic DNA immediately adjacent to either side of the inserted DNA, resulting in a new DNA molecule. This DNA molecule is created by the act of inserting the transgenic DNA into the genome of the cotton plant, i.e., by the act of transformation. This DNA molecule therefore comprises a nucleotide sequence that is both specific to the event and that is unique to the genome of the cotton plant into which the transgenic DNA has been inserted, in that this nucleotide sequence contains both the sequence of a particular region of cotton genomic DNA and of the transgenic DNA insert. The arrangement of the inserted DNA in cotton event TAM66274 in relation to the surrounding cotton plant genome DNA is therefore specific and unique for cotton event TAM66274. This DNA molecule is also an integral part of the cotton chromosome of event TAM66274 containing plants and as such is static in the plant and may be passed on to progeny of the plant.

The present invention also provides the original transformant that includes the transgene inserted into the particular location in the plant's genome and progeny of the transformant that include the transgene inserted into the particular location in the plant's genome. Such progeny may be produced by a sexual outcross between the transformant, or its progeny, and another plant. Such other plant may be a transgenic plant comprising the same or different transgene and/or a nontransgenic plant, such as one from a different variety. Even after repeated back-crossing to a recurrent parent, the inserted DNA and flanking DNA from the transformed parent is present in the progeny of the cross at the same genomic location.

As used herein, the term "cotton" means *Gossypium hirsutum* and includes all plant varieties that can be bred with cotton, including wild cotton species as well as those plants belonging to *Gossypium* that permit breeding between species.

Event TAM66274 comprises an integrated transgenic expression cassette that confers ultra-low gossypol levels in cotton seeds. Event TAM66274 has been shown to have ultra-low gossypol levels in the seed, while maintaining normal plant-protecting gossypol levels in the rest of the plant. It is believed that this phenotype is attributable to RNA interference (RNAi) mediated silencing of δ-cadinene synthase (dCS) genes that encode δ-cadinene synthase (dCS), a key enzyme (CAD1: EC 4.2.3.13, referred to as dCS) involved in gossypol biosynthesis, using a seed-specific promoter. Event TAM66274 contains an RNAi cassette for targeting the members of dCS gene family in the seed, and it is believed that tissue-specific suppression of dCS expression by RNAi causes disruption of terpenoid biosynthesis in the seed resulting in the ULGCS trait, while retaining a full complement of gossypol and other protective terpenoids in the rest of the event TAM66274 comprising plant. In one embodiment, the present event TAM66274 and resulting ULGCS will increase the value of cotton seed to farmers, with benefits to processors and end users in livestock and aquaculture industries, and ultimately consumers.

As used herein, the term "recombinant" refers to a form of DNA and/or protein and/or an organism that would not normally be found in nature and as such was created by human intervention. Such human intervention may produce a recombinant DNA molecule and/or a recombinant plant. As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the cotton genomic DNA, which may ultimately result in the expression of a recombinant RNA and/or protein molecule in that organism. As used herein, a "recombinant plant" is a plant that would not normally exist in nature, is the result of human intervention, and contains a transgene and/or heterologous DNA molecule incorporated into its genome. As a result of such genomic alteration, the recombinant plant is distinctly different from the related wildtype plant. An example of a recombinant plant is a cotton plant described herein as comprising event TAM66274.

As used herein, the term "transgene" refers to a nucleotide molecule artificially incorporated into a host cell's genome. Such transgene may be heterologous to the host cell. The term "transgenic plant" refers to a plant comprising such a transgene.

As used herein, the term "heterologous" refers to a first molecule not normally found in combination with a second molecule in nature. For example, a molecule may be derived from a first species and inserted into the genome of a second species. The molecule would thus be heterologous to the host and the host cells genome and DNA.

As used herein, the term "chimeric" refers to a single DNA molecule produced by fusing a first DNA molecule to a second DNA molecule, where neither first nor second DNA molecule would normally be found in that configuration, i.e., fused to the other. The chimeric DNA molecule is thus a new DNA molecule not otherwise normally found in nature.

The invention provides DNA molecules and their corresponding nucleotide sequences. As used herein, the term "DNA", "DNA molecule", "nucleotide molecule" refers to a DNA molecule of genomic or synthetic origin, i.e., a polymer of deoxyribonucleotide bases or a polynucleotide molecule, read from the 5' (upstream) end to the 3' (downstream) end. As used herein, the term "DNA sequence", "nucleotide sequence" or "polynucleotide sequence" refers to the nucleotide sequence of a DNA molecule. The nomenclature used herein is that required by Title 37 of the United States Code of Federal Regulations § 1.822 and set forth in the tables in WIPO Standard ST.25 (1998), Appendix 2, Tables 1 and 3. By convention, the nucleotide sequences of the invention provided as SEQ ID NO:1-7 and fragments thereof are disclosed with reference to only one strand of the two complementary nucleotide sequence strands. By implication, the complementary sequences (i.e. the sequences of the complementary strand), also referred to in the art as the reverse complementary sequences, are within the scope of the invention and are expressly intended to be within the scope of the subject matter claimed.

The nucleotide sequence corresponding to the complete nucleotide sequence of the inserted transgenic DNA and substantial segments of the cotton genome DNA flanking either end of the inserted transgenic DNA is provided herein as SEQ ID NO:4. A subsection of this, also comprising the complete nucleotide sequence of the inserted transgenic DNA and shorter segments of the flanking cotton genome, is provided as SEQ ID NO:3.

Figure 1:
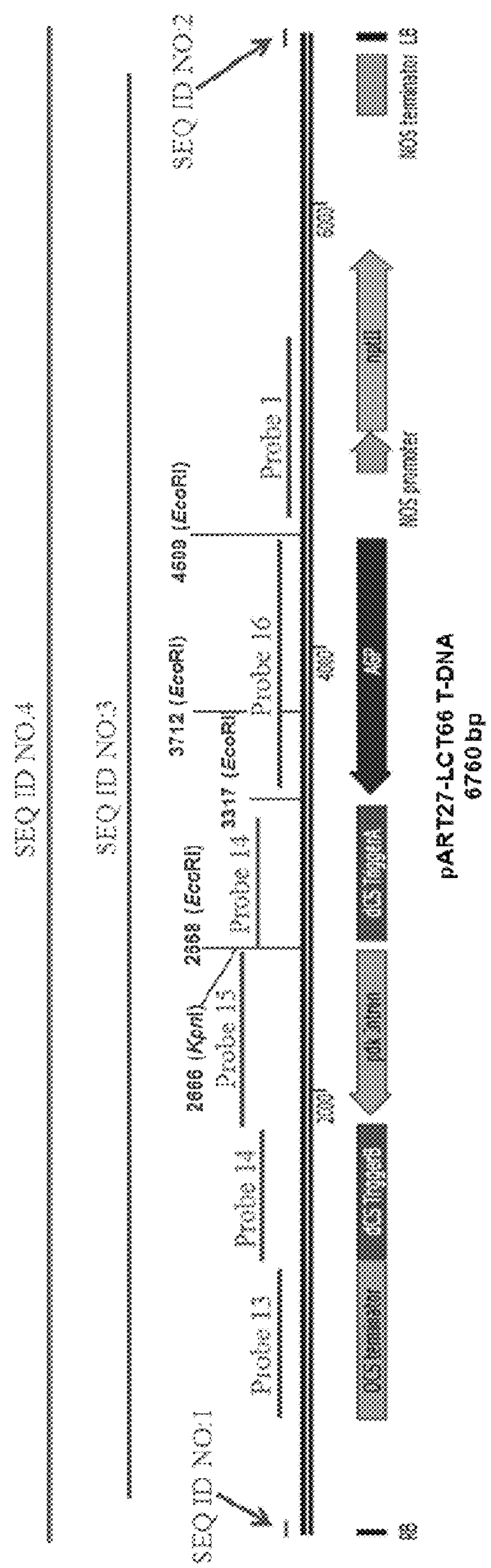
FIG. 1 illustrates the organization of the transgenic insert in the genome of a cotton plant comprising event TAM66274. The relative positions of SEQ ID NO:1-4 are shown, as well as the relative positions of Probes 1, 13, 14, 15, and 16. Also shown are the sites for two restriction enzymes (EcoRI and KpnI) that were used to cut the genomic DNA for Southern blot analyses.

The cotton event TAM66274 further comprises two regions, one spanning the 5' location and one spanning the 3' location where the transgenic DNA is inserted into the genomic DNA, referred to herein as the 5' and 3' junction, respectively. A "junction sequence" or "junction region" refers to the DNA sequence and/or corresponding DNA molecule that spans the inserted transgenic DNA and the adjacent flanking genomic DNA. The junction sequences may be arbitrarily represented by the nucleotide sequences provided as SEQ ID NO:1 and SEQ ID NO:2, each representing 200 bp of the flanking genomic DNA adjacent to and contiguous with 200 bp of insert DNA. These nucleotides are connected by phosphodiester linkage and in cotton event TAM66274 are present as part of the genome. The identification of one or more of SEQ ID NO:1-4 in a sample derived from a cotton plant, seed, or plant part is determinative that the DNA was obtained from cotton event TAM66274 and is diagnostic for the presence in a sample of DNA from cotton event TAM66274. The invention thus provides a DNA molecule that contains at least one of the nucleotide sequences provided as SEQ ID NO:1-4. Any segment of DNA derived from transgenic cotton event TAM66274 that is sufficient to include at least one of the sequences provided as SEQ ID NO:1-4 is within the scope of the invention. In addition, any polynucleotide comprising a sequence complementary to any of the sequences described within this paragraph is within the scope of the invention. FIG. 1 illustrates the physical arrangement of SEQ ID NO:1-4 relative to one another and arranged from 5' to 3'.

The invention provides exemplary DNA molecules that can be used either as primers or probes for diagnosing the presence of DNA derived from a cotton plant comprising event TAM66274 in a sample. Such primers or probes are specific for a target nucleic acid sequence and as such are useful for the identification of cotton event TAM66274 nucleic acid sequence by the methods of the invention described herein.

A "primer" is typically a highly purified, isolated polynucleotide that is designed for use in specific annealing or hybridization methods that involve thermal amplification. A pair of primers may be used with template DNA, such as a sample of cotton genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques. An amplicon of the invention comprises at least one of the sequences provided as SEQ ID NO:1-4. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO:6-7. The primer pair provided as SEQ ID NO:6 and SEQ ID NO:7 are useful as a first DNA molecule and a second DNA molecule that is different from the first DNA molecule, and both are each of sufficient length of contiguous nucleotides of SEQ ID NO:4 to function as DNA primers that, when used together in a thermal amplification reaction with template DNA derived from cotton event TAM66274, to produce an amplicon diagnostic for cotton event TAM66274 DNA in a sample.

A "probe" is an isolated nucleic acid that is complementary to a strand of a target nucleic acid. Probes according to the invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from cotton event TAM66274 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: Nucleic Acid Hybridization, A Practical Approach, IRL Press, Washington, D.C. (1985). As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, two molecules exhibit "complete complementarity" if when aligned, every nucleotide of the first molecule is complementary to every nucleotide of the second molecule. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Departures from complete complementarity are therefore permissible, as long as such departures do not completely preclude the capacity of the molecules to form a double-stranded structure.

Appropriate stringency conditions that promote DNA hybridization are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In one embodiment, a polynucleic acid of the present invention will specifically hybridize to one or more of the nucleic acid molecules set forth in SEQ ID NOs: 1, 2, 3, or 4, or complements thereof or fragments of either under moderately stringent conditions, for example at about 2.0×SSC and about 65° C. In another embodiment, a nucleic acid of the present invention will specifically hybridize to one or more of the nucleic acid molecules set forth in SEQ ID NOs: 1, 2, 3, or 4, or complements or fragments of either under high stringency conditions.

As used herein, the term "isolated" refers to at least partially separating a molecule from other molecules normally associated with it in its native or natural state. In one embodiment, the term "isolated" refers to a DNA molecule that is at least partially separated from the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying cotton event TAM66274, selecting plant varieties or hybrids comprising cotton event TAM66274, detecting the presence of DNA derived from the transgenic cotton event TAM66274 in a sample, and monitoring samples for the presence and/or absence of cotton event TAM66274 or plant parts derived from cotton plants comprising event TAM66274.

The invention provides cotton plants, progeny, seeds, plant cells, plant parts (such as pollen, ovule, pod, flower tissue, root tissue, stem tissue, and leaf tissue), and commodity products. These plants, progeny, seeds, plant cells, plant parts, and commodity products contain a detectable amount of a polynucleotide of the invention, i.e., such as a polynucleotide having at least one of the sequences provided as SEQ ID NO:1-4. Plants, progeny, seeds, plant cells, and plant parts of the invention may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, ultra-low gossypol levels in cotton seeds, and/or increased herbicide tolerance, in which the desirable trait is measured with respect to a cotton plant lacking such additional transgene.

The invention provides cotton plants, progeny, seeds, plant cells, and plant part such as pollen, ovule, pod, flower, root or stem tissue, and leaves derived from a transgenic cotton plant comprising event TAM66274. A representative sample of cotton seed comprising event TAM66274 has been deposited according to the Budapest Treaty with the American Type Culture Collection (ATCC®). The ATCC repository has assigned the Patent Deposit Designation PTA-124218 to the event TAM66274 comprising seed.

The invention provides a microorganism comprising a DNA molecule having at least one sequence selected from SEQ ID NO:1-4 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event DNA, including the transgene, to progeny. As used herein, "progeny" includes any plant, seed, plant cell, and/or regenerable plant part comprising the event DNA derived from an ancestor plant and/or comprising a DNA molecule having at least one sequence selected from SEQ ID NO:1-4. Plants, progeny, and seeds may be homozygous or heterozygous for the transgene. Progeny may be grown from seeds produced by a cotton event TAM66274 containing plant and/or from seeds produced by a plant fertilized with pollen from a cotton event TAM66274 containing plant.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be outcrossed, e.g., bred with another unrelated plant, to produce a varietal or a hybrid seed or plant. The other unrelated plant may be transgenic or nontransgenic. A varietal or hybrid seed or plant of the invention may thus be derived by crossing a first parent that lacks the specific and unique DNA of the cotton event TAM66274 with a second parent comprising cotton event TAM66274, resulting in a hybrid comprising the specific and unique DNA of the cotton event TAM66274. Each parent can be a hybrid or an inbred/varietal, so long as the cross or breeding results in a plant or seed of the invention, i.e., a seed having at least one allele containing the DNA of cotton event TAM66274 and/or a DNA molecule having at least one sequence selected from SEQ ID NO:1-4. Two different transgenic plants may thus be crossed to produce hybrid offspring that contain two independently segregating, added, exogenous genes. For example, the event TAM66274 exhibiting ultra-low gossypol levels in cotton seeds can be crossed with other transgenic cotton plants to produce a plant having the characteristics of both transgenic parents. One example of this would be a cross of event TAM66274 containing ultra-low gossypol level cotton seeds with a plant having one or more additional traits such as herbicide tolerance and/or insect control, resulting in a progeny plant or seed that has ultra-low gossypol levels in cotton seeds and has at least one or more additional traits. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

The invention provides a plant part that is derived from cotton plants comprising event TAM66274. As used herein, a "plant part" refers to any part of a plant which is comprised of material derived from a cotton plant comprising event TAM66274. Plant parts include but are not limited to pollen, ovule, pod, flower, root or stem tissue, fibers, and leaves. Plant parts may be viable, nonviable, regenerable, and/or nonregenerable.

The invention provides a commodity product that is derived from cotton plants comprising event TAM66274. As used herein, a "commodity product" refers to any composition or product which is comprised of material derived from a cotton event TAM66274 containing plant, seed, plant cell, or plant part. Commodity products may be sold to consumers and may be viable or nonviable. Nonviable commodity products include but are not limited to nonviable seeds, processed seeds, seed parts, and plant parts, lint, seeds and plant parts processed for feed or food, oil, fiber, paper, biomasses, and fuel products. Viable commodity products include but are not limited to seeds, plants, and plant cells. The cotton plants comprising event TAM66274 can thus be used to manufacture any commodity product typically acquired from cotton. Any such commodity product that is derived from cotton plants comprising event TAM66274 may contain at least a detectable amount of the specific and unique DNA corresponding to cotton event TAM66274, and specifically may contain a detectable amount of a polynucleotide comprising a DNA molecule having at least one sequence selected from SEQ ID NO:1-4. Any standard method of detection for nucleotide molecules may be used, including methods of detection disclosed herein. A commodity product is within the scope of the invention if there is any detectable amount of a DNA molecule having at least one sequence selected from SEQ ID NO:1-4 in the commodity product.

As used herein, the term "ultra-low gossypol level" in seeds or "ULGCS" means levels that would be fit for consumption by humans or monogastric animals, i.e., lower than the maximum allowable level of 450 ppm that is considered safe for modified cotton seed products in foods for human consumption (FDA, 1960; FDA, 1972; FDA, 1976) and below 400 ppm allowed in low-gossypol cotton seed meal used as animal feed (AAFCO, 1968a; AAFCO, 1968b).

The plants, progeny, seeds, plant cells, plant parts (such as pollen, ovule, pod, flower, root or stem tissue, and leaves), and commodity products of the invention are therefore useful for, among other things, growing plants for the purpose of producing seed and/or plant parts comprising cotton event TAM66274 for agricultural purposes, producing progeny comprising cotton event TAM66274 for plant breeding and research purposes, use with microbiological techniques for industrial and research applications, and sale to consumers.

The invention provides methods for producing plants using cotton event TAM66274. Methods for producing a ultra-low gossypol level cotton seed plant comprising the DNA sequences specific and unique to event TAM66274 of the invention are provided, as described herein. Transgenic plants used in these methods may be homozygous or heterozygous for the transgene. Progeny plants produced by these methods may be varietal or hybrid plants; may be grown from seeds produced by a cotton event TAM66274 containing plant and/or from seeds produced by a plant fertilized with pollen from a cotton event TAM66274 containing plant; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant.

A cotton plant that exhibits ultra-low gossypol levels in cotton seeds may be produced by sexually crossing an event TAM66274 containing plant comprising a DNA molecule having at least one sequence selected from SEQ ID NO:1-4 with another cotton plant and thereby producing seed, which is then grown into progeny plants. These progeny plants may be analyzed using diagnostic methods to select for progeny plants that contain the event TAM66274 DNA. The other plant used in the crossing may or may not exhibit ultra-low gossypol seed level and may or may not be transgenic. The progeny plant and/or seed produced may be varietal or hybrid seed. In practicing this method, the step of sexually crossing one plant with another plant, i.e., cross-pollinating, may be accomplished or facilitated by human intervention, for example: by human hands collecting the pollen of one plant and contacting this pollen with the style or stigma of a second plant; by human hands and/or actions removing, destroying, or covering the stamen or anthers of a plant (e.g., by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma; by selective placement of plants (e.g., intentionally planting plants in pollinating proximity); and/or by application of chemicals to precipitate flowering or to foster receptivity (of the stigma for pollen).

A cotton plant that exhibits ultra-low gossypol levels in cotton seeds may be produced by selfing an event TAM66274 containing plant comprising a DNA molecule having at least one sequence selected from SEQ ID NO:1-4 and thereby producing seed, which is then grown into progeny plants. These progeny plants may be analyzed using diagnostic methods to select for progeny plants that contain the event TAM66274 DNA. In practicing this method, the step of sexually crossing one plant with itself, i.e., self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (e.g., by application of a chemical gametocide) so that natural cross-pollination is prevented and self-pollination would have to take place in order for fertilization to occur; by human placement of pollinating insects in a position for "directed pollination" (e.g., by caging a plant alone with pollinating insects); by human manipulation of the flower or its parts to allow for self-pollination; by selective placement of plants (e.g., intentionally planting plants beyond pollinating proximity); and/or by application of chemicals to precipitate flowering or to foster receptivity (of the stigma for pollen).

Progeny cotton plants and seeds encompassed by these methods and produced by using these methods will be distinct from other cotton plants, for example, because the progeny cotton plants and seeds: are recombinant and as such created by human intervention; exhibit ultra-low gossypol levels in cotton seeds; contain at least one allele that consists of the transgene DNA of the invention; and/or contain a detectable amount of a DNA molecule comprising at least one sequence selected from SEQ ID NO:1-4. A seed may be selected from an individual progeny plant, and so long as the seed comprises a DNA molecule having at least one sequence selected from SEQ ID NO:1-4, it will be within the scope of the invention.

In practicing the invention, two different transgenic plants can be crossed to produce hybrid offspring that contain two independently segregating heterologous genes. Selfing of appropriate progeny can produce plants that are homozygous for both genes. Back-crossing to a parental plant and out-crossing with a non-transgenic plant are also contemplated, as is vegetative propagation. Descriptions of other methods that are commonly used for different traits and crops can be found in one of several references, e.g., Fehr, in Breeding Methods for Cultivar Development, Wilcox J. ed., American Society of Agronomy, Madison Wis. (1987).

The plants and seeds used in the methods disclosed herein may also contain one or more additional transgenes. Such transgene may be any nucleotide sequence encoding a protein or RNA molecule conferring a desirable trait including but not limited to herbicide tolerance, increased insect resistance, increased water use efficiency, increased yield performance, increased drought resistance, increased seed quality, improved nutritional quality, and/or ultra-low gossypol levels in cotton seeds, in which the desirable trait is measured with respect to a cotton plant lacking such additional transgene.

The methods of the invention are therefore useful for, among other things, growing plants for the purpose of producing seed and/or plant parts comprising cotton event TAM66274 for agricultural or research purposes, selecting for progeny comprising cotton event TAM66274 for plant breeding or research purposes, and producing progeny plants and seeds comprising cotton event TAM66274.

The plants, progeny, seeds, plant cells, plant parts (such as pollen, ovule, pod, flower, root or stem tissue, and leaves), and commodity products of the invention may be evaluated for DNA composition, gene expression, and/or protein expression. Such evaluation may be done by using any standard method such as PCR, northern blotting, southern analysis, western blotting, immuno-precipitation, and ELISA or by using the methods of detection and/or the detection kits provided herein.

Methods of detecting the presence of DNA derived from a cotton cell, tissue, seed, or plant comprising cotton event TAM66274 in a sample are provided. One method consists of (i) extracting a DNA sample from at least one cotton cell, tissue, seed, or plant, (ii) contacting the DNA sample with at least one primer that is capable of producing DNA sequence specific to event TAM66274 DNA under conditions appropriate for DNA sequencing, (iii) performing a DNA sequencing reaction, and then (iv) confirming that the nucleotide sequence comprises a nucleotide sequence specific for event TAM66274, such as one selected from the group consisting of SEQ ID NO:1-4. Another method consists of (i) extracting a DNA sample from at least one cotton cell, tissue, seed, or plant, (ii) contacting the DNA sample with a primer pair that is capable of producing an amplicon from event TAM66274 DNA under conditions appropriate for DNA amplification, (iii) performing a DNA amplification reaction, and then (iv) detecting the amplicon molecule and/or confirming that the nucleotide sequence of the amplicon comprises a nucleotide sequence specific for event TAM66274, such as one selected from the group consisting of SEQ ID NO:1-4. The amplicon should be one that is specific for event TAM66274. The detection of a nucleotide sequence specific for event TAM66274 in the amplicon is determinative and/or diagnostic for the presence of the cotton event TAM66274 specific DNA in the sample. An example of a primer pair that is capable of producing an amplicon from event TAM66274 DNA under conditions appropriate for DNA amplification is provided as SEQ ID NO:6-7. Other primer pairs may be readily designed by one of skill in the art and would comprise at least one fragment of SEQ ID NO:4. Another method of detecting the presence of DNA derived from a cotton cell, tissue, seed, or plant comprising cotton event TAM66274 in a sample consists of (i) extracting a DNA sample from at least one cotton cell, tissue, seed, or plant, (ii) contacting the DNA sample with a DNA probe specific for event TAM66274 DNA, (iii) allowing the probe and the DNA sample to hybridize under stringent hybridization conditions, and then (iv) detecting hybridization between the probe and the target DNA sample. Other probes may be readily designed by one of skill in the art and would comprise at least one fragment of SEQ ID NO:4. Detection of probe hybridization to the DNA sample is diagnostic for the presence of cotton event TAM66274 specific DNA in the sample. Absence of hybridization is alternatively diagnostic of the absence of cotton event TAM66274 specific DNA in the sample.

DNA detection kits are provided that are useful for the identification of cotton event TAM66274 DNA in a sample and can also be applied to methods for breeding cotton plants containing the appropriate event DNA. Such kits may contain DNA primers and/or probes comprising fragments of SEQ ID NO:1-7. A DNA detection kit may also comprise instructions for use of the kit. One example of such a kit comprises at least one DNA molecule of sufficient length of contiguous nucleotides of SEQ ID NO:4 to function as a DNA probe useful for detecting the presence and/or absence of DNA derived from transgenic cotton plants comprising event TAM66274 in a sample. The DNA derived from transgenic cotton plants comprising event TAM66274 would comprise a DNA molecule having at least one sequence selected from SEQ ID NO:1-4. Other probes may be readily designed by one of skill in the art and should comprise at least 15 contiguous nucleotides of SEQ ID NO:4 and be sufficiently unique to cotton event TAM66274 DNA in order to identify DNA derived from the event. Another type of kit comprises a primer pair useful for producing an amplicon useful for detecting the presence and/or absence of DNA derived from transgenic cotton event TAM66274 in a sample. Such a kit would employ a method comprising contacting a target DNA sample with a primer pair as described herein, then performing a nucleic acid amplification reaction sufficient to produce an amplicon comprising a DNA molecule having at least one sequence selected from SEQ ID NO:1-4, 6, or 7, and then detecting the presence and/or absence of the amplicon. Such a method may also include sequencing the amplicon or a fragment thereof, which would be determinative of, i.e. diagnostic for, the presence of the cotton event TAM66274 specific DNA in the target DNA sample. Other primer pairs may be readily designed by one of skill in the art and should comprise at least 15 contiguous nucleotides of SEQ ID NO:4 and be sufficiently unique to cotton event TAM66274 DNA in order to identify DNA derived from the event.

Nucleic-acid amplification can be accomplished by any of the various nucleic-acid amplification methods known in the art, including thermal amplification methods. Many techniques are known in the art for detecting, quantifying, and/or sequencing the amplicon produced by these methods. One exemplary technique useful in practicing this invention is TAQMAN® (PE Applied Biosystems, Foster City, Calif.).

The kits and detection methods of the invention are useful for, among other things, identifying cotton event TAM66274, selecting plant varieties or hybrids comprising cotton event TAM66274, detecting the presence of DNA derived from the transgenic cotton plants comprising event TAM66274 in a sample, and monitoring samples for the presence and/or absence of cotton plants comprising event TAM66274 or plant parts derived from cotton plants comprising event TAM66274.

The sequence of the heterologous DNA insert, junction sequences, or flanking sequences from cotton event TAM66274 can be verified (and corrected if necessary) by amplifying such sequences from the event using primers derived from the sequences provided herein followed by standard DNA sequencing of the amplicon or of the cloned DNA.

As used herein, the term "comprising" means "including but not limited to".

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Cotton and Event TAM66274 Selection

This example describes the production, analysis, and selection of event TAM66274. Summarized is the production and analysis of hundreds of individual plants over multiple years through the rigorous molecular, phenotypic, and field testing required for the ultimate selection of the TAM66274 event.

Production of Event TAM66274

The transgenic TAM66274 event, which exhibits ultra-low levels of the anti-nutrient gossypol in the cotton seed, was generated by *Agrobacterium tumefaciens*-mediated transformation of cotton tissues from non-transgenic cv. Coker 312 utilizing a plant transformation vector comprising the expression cassette illustrated in FIG. 1. Methods for transforming cotton are known in the art. To produce the TAM66274 event, non-transgenic cv. Coker 312 cotton materials was used for plant transformation. Cotton cells were transformed and regenerated into intact cotton plants. Rooted plants with normal phenotypic characteristics were selected and transferred to soil for growth and further assessment.

Figure 2:
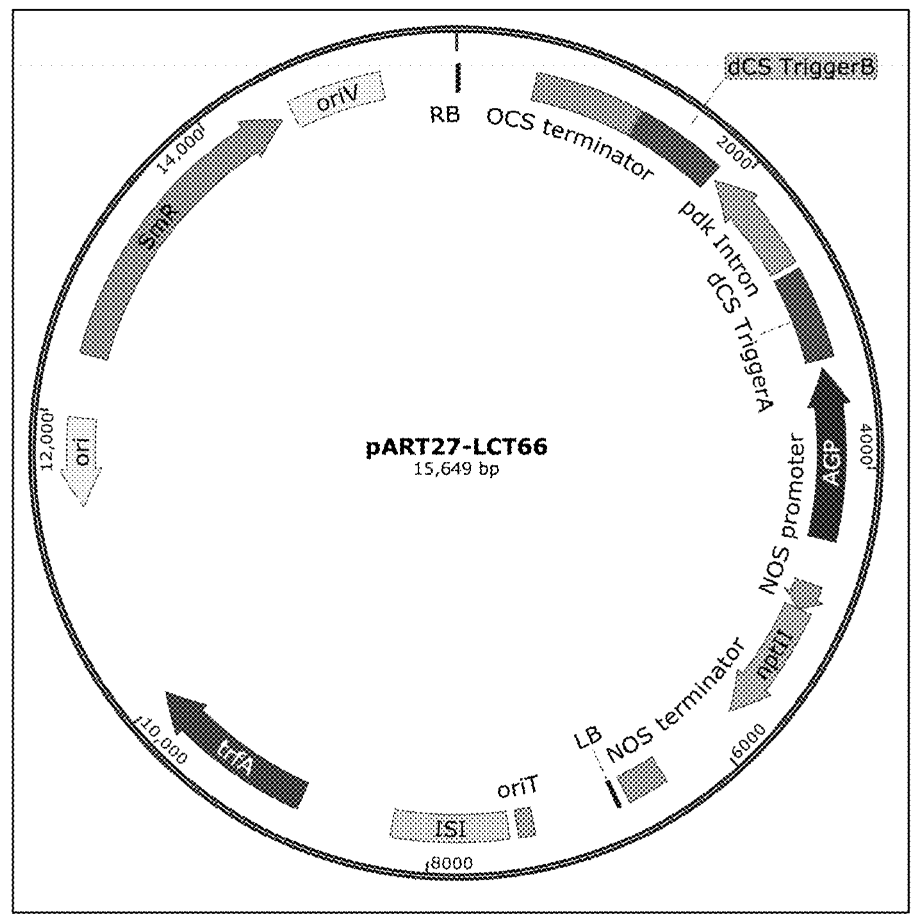
FIG. 2 shows the circular map of the binary vector pART27-LCT66.

Plasmid pART27-LCT66, shown in FIG. 2, is approximately 15.6 kilobase (kb). The backbone DNA sequences of pART27-LCT66 are based on the pART-27 binary vector. The transfer DNA (T-DNA) region of pART27-LCT66 contains a dCS silencing cassette and a nptII expression cassette, which is delineated by the right border (RB) and left border (LB) repeat sequences.

The 6.8 kb T-DNA region of plasmid pART27-LCT66 has two gene cassettes: a dCS RNAi cassette and a nptII expression cassette. The organization and orientation of these two cassettes are depicted in a linear map, as shown in FIG. 1. The dCS RNAi cassette is designed to silence the endogenous dCS genes in cotton seed. It is comprised of a highly seed-specific AGP derived from cotton (*G. hirsutum*), a 604 bp internal sequence (Trigger A) of the dCS gene from cotton (*G. hirsutum*), an intron from the pyruvate dehydrogenase kinase (pdk) gene from *Flaveria trinervia*, a reverse complement of the Trigger A sequence (Trigger B) and the terminator sequence of the octopine synthase (ocs) gene from *A. tumefaciens*.

The putative AGP, comprised of 1108 bp of the promoter sequence and a 36 bp 5'-untranslated region (UTR) of the cotton α-globulin B gene, was isolated by genome walking. The seed-specificity of the AGP, and its suitability for use in silencing dCS genes in cotton seed but not in other plant parts, was verified in studies before the development of event TAM66274. In brief, the AGP region was fused to the β-glucuronidase (gusA) reporter gene in the binary vector pBI101.3 (Clontech) and the construct was used to determine promoter activity in transgenic cotton plants.

dCS catalyzes the first committed step involving the cyclization of FDP to (+)-δ-cadinene. The dCS is encoded by a gene family that is divided into two subfamilies, CAD1-A and CAD1-C(Cdn1-C1, Cdn1-C14, Cdn1-A, and Cdn1-C2) based on sequence similarities. Others have previously confirmed that the dCS gene belongs to the CAD1-C subfamily. The diploid genome of *G. arboreum* contains about six members of CAD1-C and a single copy of CAD1-A. Starting at 23 dpa, dCS transcripts increase dramatically in the developing embryo, closely followed by enzyme activity and gossypol accumulation. By probing a cDNA library, prepared from the mRNA obtained from developing *G. hirsutum* embryos, with the *G. arboreum*-derived cad1-C1 gene (Genbank accession #AF174294), a clone of the dCS gene has previously been isolated. A 604 bp internal fragment amplified from this cDNA clone was used as the trigger A sequence and a reverse complement of the Trigger A sequence (Trigger B) to make an ihp RNA construct using the pHANNIBAL/pART27 system. The expression of this cassette results in formation of a dsRNA transcript corresponding to a segment of the dCS genes in cotton. The dsRNA is recognized and processed by the cotton plant's RNAi machinery, resulting in suppression of dCS enzyme activity.

The selected trigger A sequence has 80.9-99.8% homology to several other published sequences of dCS genes from the diploid (*G. arboreum*) and tetraploid (*G. hirsutum*) cottons. This sequence was intended to target all members of the dCS gene family, including cad1-A, because it bears several stretches (20-35 bp) of perfect homology to the selected sequence. AGP was used to control the expression of this ihp RNA sequence, thereby restricting the silencing of dCS gene(s) to the seed tissue only.

The selectable marker gene used to generate event TAM66274 was the nptII gene. The nptII expression cassette serves as a plant selectable marker gene cassette. This gene was isolated from the *Escherichia coli* Tn5 transposon and encodes the enzyme neomycin phosphotransferase type II (NPTII), which confers resistance to the antibiotics kanamycin and neomycin. NPTII uses adenosine triphosphate (ATP) to phosphorylate kanamycin and neomycin, thereby inactivating the antibiotic and preventing it from killing the NPTII-producing cell. The NPTII expression cassette consists of the promoter and 3'-UTR sequences from the nopaline synthase (nos) gene of *A. tumefaciens* and the nptII gene derived from *E. coli* Tn5. The NPTII expression cassette in pART27 was derived from pGA643. Expression of the NPTII gene renders transformed cells resistant to the antibiotic (kanamycin), thus allowing selection of transformed cells in tissue culture.

Analysis and Selection of Event TAM66274

In two rounds of transformation experiments, 346 individual transgenic events were generated and grown in a greenhouse. Kernels from T1 seeds obtained from 188 individual transgenic healthy and fertile events were first examined visually for the color of glands, a reliable indicator of gossypol levels. Seeds from 43 individual transgenic events thus selected were subjected to gossypol analysis. Null segregating seeds (dark colored glands in the kernel) were discarded and transgene containing pooled T1 seeds (homozygous and hemizygous) were used for gossypol determination using the HPLC method. These transgenic events were also examined for the integration of the transgene cassette and copy numbers by Southern blot analysis. Some individual transgenic events that had single transgene copy integration and low seed gossypol values were selected for preliminary, small-scale field trials. Events TAM6649B, TAM66103, TAM66163C, TAM66193B, TAM66239, TAM66250, TAM66274, TAM66316, and TAM66317 were examined. Transgenic event TAM6681 had multiple transgene copies integrated into its genome and was also tested. Based on their performance, transgenic events TAM6649B and TAM66274 were selected for further assessment. This required an extensive, molecular and biochemical characterization of these two events as well as multi-location field trials. While conducting detailed molecular characterization of these two events, it was discovered that event TAM6649B had one full and a partial copy of the T-DNA integrated into its genome. In addition, this event performed poorly in terms of fiber and seed yield in the multi-location field trials, so it was dropped from further assessment. The transgenic event TAM66274 was moved forward for deregulation. As described herein, transgenic event TAM66274 exhibits ultra-low gossypol levels in seeds while maintaining normal gossypol levels in other plant tissues.

Example 2

Characterization of Event TAM66274 DNA Sequences

This example describes the molecular characterization of the TAM66274 event. The DNA inserted into the genome of cotton plants comprising event TAM66274 and the genomic sequence flanking this insertion were characterized by detailed molecular analyses. These analyses included: the insert sequence, the insert number (number of integration sites within the cotton genome), the copy number (number of copies of transgene DNA within one locus), the integrity of the inserted gene cassette, the flanking sequences, and the association of the insertion with haplotype regions of the cotton genome.

Molecular DNA probes were used that included the intact coding region and its respective regulatory elements, the promoters, introns, and polyadenylation sequences of the plant expression cassettes.

Southern Blot Analyses of the T-DNA Insert in Event TAM66274

Figure 3:
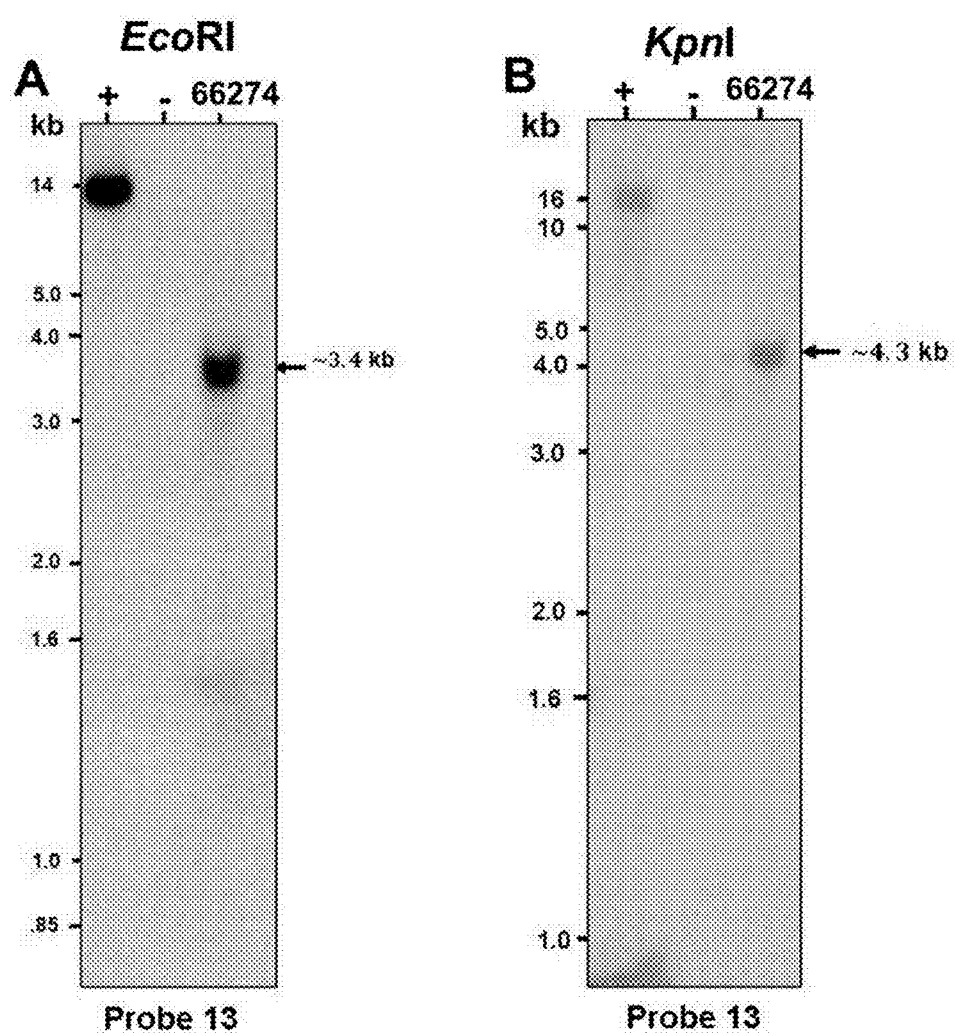
FIG. 3 demonstrates RB T-DNA integration in event TAM66274 using Southern Blot Analysis. Approximately 12 μg of genomic DNA was digested with EcoRI (A) or KpnI (B) and loaded per lane. Positive controls included EcoRI digested (A) or KpnI digested (B) pART27-LCT66 plasmid at approximately one copy equivalent per cotton genome mixed with 12 μg of genomic DNA extracted from non-transgenic cv. Coker 312. The negative control included genomic DNA from non-transgenic cv. Coker 312. Fragment sizes are shown in kb. The membrane was hybridized with radiolabeled ocs terminator sequence (Probe 13). The lane marked (+) is the positive control; the lane marked (−) is negative control; and the lane marked 66274 is event TAM66274.
Figure 4:
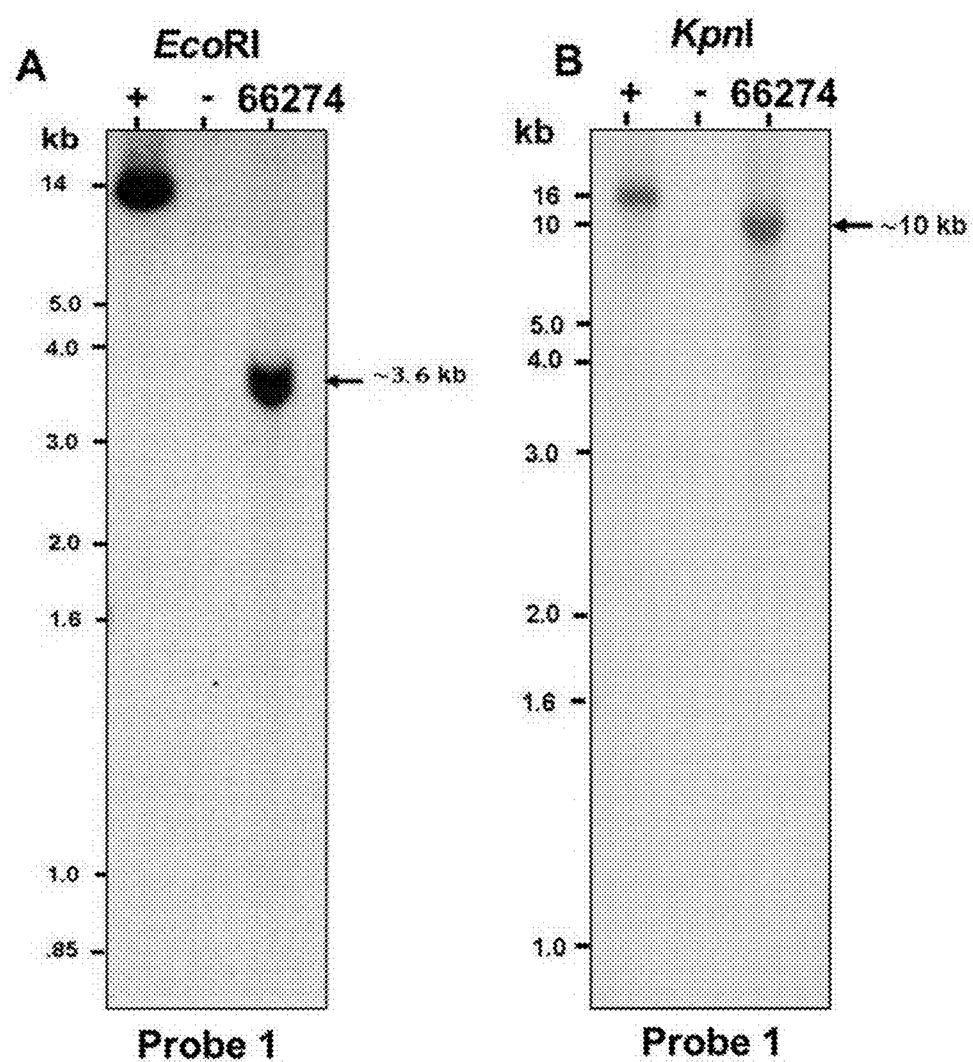
FIG. 4 shows LB T-DNA integration in event TAM66274 using Southern Blot Analysis. Approximately 12 μg of genomic DNA was digested with EcoRI (A) or KpnI (B) and loaded per lane. Positive controls included EcoRI digested (A) or KpnI digested (B) pART27-LCT66 plasmid at approximately one copy equivalent per cotton genome mixed with 12 μg of genomic DNA extracted from non-transgenic cv. Coker 312. The negative control included genomic DNA from non-transgenic cv. Coker 312. Fragment sizes are shown in kb. The membrane was hybridized with radiolabeled nos promoter+nptII sequence (Probe 1). The lane marked (+) is the positive control; the lane marked (−) is negative control; and the lane marked 66274 is event TAM66274.
Figure 5:
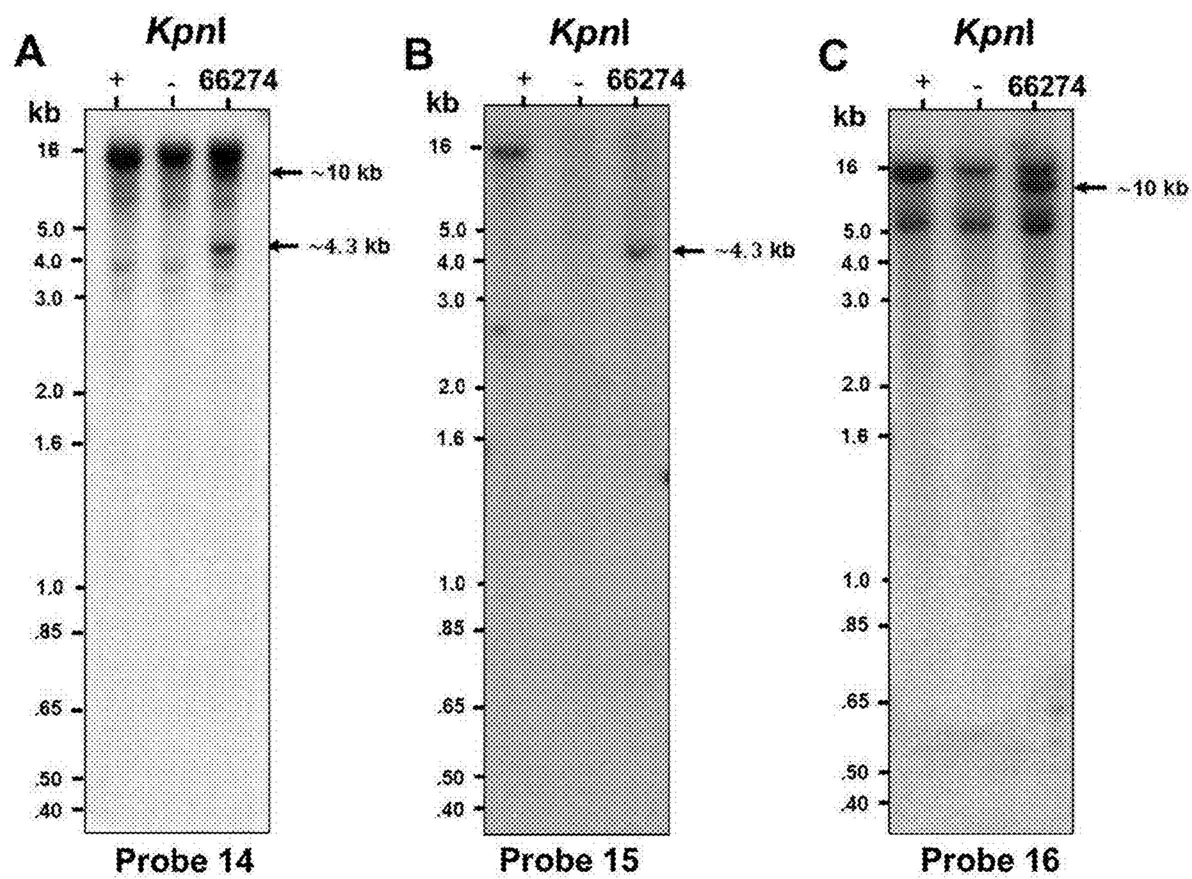
FIG. 5 shows integration of the internal genetic elements of the T-DNA in event TAM66274 using Southern blot analyses. Approximately 12 μg of genomic DNA was digested with KpnI and loaded per lane. The positive control included KpnI digested pART27-LCT66 plasmid at approximately one copy equivalent per cotton genome mixed with 12 μg of genomic DNA extracted from non-transgenic cv. Coker 312. The negative control included genomic DNA from non-transgenic cv. Coker 312. Fragment sizes are shown in kb. The membrane was hybridized with radiolabeled (A) δ-cadinene synthase (dCS) trigger (Probe 14), (B) pdk intron (Probe 15) or (C) AGP (Probe 16). The lane marked (+) is the positive control; the lane marked (−) is negative control; and the lane marked 66274 is event TAM66274.

To interpret the results of Southern blot analyses, linear maps of the binary vector showing the location of each specific probe and restriction enzyme sites are provided in FIG. 1 which serves as a guide for the blots shown in FIGS. 3, 4, and 5. In addition, comparisons of the expected and observed hybridization bands are presented in Tables 1-3. In the tables and figures corresponding to the Southern blots, the sizes of the hybridization bands are rounded to the nearest tenth and expressed in kb.

RB Integration in Event TAM66274

The RB integration pattern of T-DNA in event TAM66274 was investigated by Southern blot analysis. Approximately 12 μg of genomic DNA was digested with EcoRI (A) or KpnI (B) and loaded per lane. Positive controls included EcoRI digested (A) or KpnI digested (B) pART27-LCT66 plasmid at approximately one copy equivalent per cotton genome mixed with 12 μg of genomic DNA extracted from non-transgenic cv. Coker 312. The negative control included genomic DNA from non-transgenic cv. Coker 312. The membrane was hybridized with radiolabeled ocs terminator sequence (Probe 13). The lane marked (+) is the positive control; the lane marked (−) is negative control; and the lane marked 66274 is event TAM66274. With restriction enzyme EcoRI and probe combination, any hybridizing band >2668 bp is considered a transgene integration in the cotton genome. As observed in the Southern blot (shown in FIG. 3A, Table 1), a single hybridization band of ~3.4 kb size was observed in event TAM66274. The size of this hybridizing band is consistent with the production of a single DNA fragment defined by the EcoRI restriction site at bp 2668 within the T-DNA and a potential EcoRI site upstream in the genomic cotton DNA flanking the 5' end of the T-DNA insert. This Southern blot thus confirmed integration of the ocs terminator region at the 5' end of the T-DNA in event TAM66274. Probe 13 hybridized with the positive control, EcoRI digest of the plasmid pART27-LCT66, and produced a hybridizing band of 13.8 kb, shown in FIG. 3A. No hybridizing bands were observed with the EcoRI digest of genomic DNA from non-transgenic cv. Coker 312.

The RB integration pattern of T-DNA in event TAM66274 was further confirmed by an additional Southern blot analysis. Genomic DNA from event TAM66274 was digested with the restriction enzyme KpnI, followed by hybridization with Probe 13 (FIG. 3B). With this restriction enzyme and probe combination, any hybridizing band >2666 bp is considered a transgene integration in the cotton genome. A single hybridization band of ~4.3 kb size was observed in event TAM66274 (FIG. 3B). The size of this hybridizing band is consistent with the production of a single DNA fragment defined by the KpnI restriction site at bp 2666 within the T-DNA (FIG. 1) and a potential KpnI site upstream in the cotton genomic DNA flanking the 5' end of the T-DNA insert. Thus, the results from this Southern blot are consistent with those from the EcoRI/Southern blot (FIG. 3A) showing that the RB region of the T-DNA integrated at a single locus in event TAM66274. Probe 13 also hybridized with the positive control, KpnI digest of the plasmid pART27-LCT66, and produced a hybridizing band of 16.0 kb (FIG. 3B). The size of this hybridizing band is consistent with the production of a single DNA fragment defined by the single KpnI restriction site at bp 2666 in the plasmid and, therefore, is the complete linearized plasmid pART27-LCT66. Further, no hybridizing bands were observed with Probe 13 for the KpnI digest of genomic DNA from non-transgenic cv. Coker 312.

TABLE 1

RB T-DNA integration analysis.
Size(s) of the expected and observed hybridization bands in event TAM66274.
RB T-DNA integration - event TAM66274

| Restriction enzyme and position | Probe | SEQ ID NO and size (bp) | Expected band(s) (kb) | Observed band(s) (kb) | Expected band for the positive control plasmid (kb) |
|---|---|---|---|---|---|
| EcoRI (2668) | 13 | SEQ ID NO: 9 523-1230 (708) | >2.7 | ~3.4 | 14.0 |
| KpnI (2666) | 13 | SEQ ID NO: 9 523-1230 (708) | >2.7 | ~4.3 | 16.0 |

LB Integration in Event TAM66274

The LB integration pattern of T-DNA in event TAM66274 was investigated by Southern blot analysis. Genomic DNA from event TAM66274 was digested with EcoRI restriction enzyme, followed by hybridization with Probe 1 that corresponds to the nos promoter and part of the nptII coding sequence. Approximately 12 μg of genomic DNA was digested with EcoRI (A) or KpnI (B) and loaded per lane. Positive controls included EcoRI digested (A) or KpnI digested (B) pART27-LCT66 plasmid at approximately one copy equivalent per cotton genome mixed with 12 μg of genomic DNA extracted from non-transgenic cv. Coker 312. The negative control included genomic DNA from non-transgenic cv. Coker 312. Fragment sizes are shown in kb. The membrane was hybridized with radiolabeled nos promoter+nptII sequence (Probe 1). The lane marked (+) is the positive control; the lane marked (−) is negative control; and the lane marked 66274 is event TAM66274.

With restriction enzyme EcoRI and probe combination, any hybridizing band >2252 bp is considered an integration in the cotton genome. A single hybridization band of ~3.6 kb size was observed in event TAM66274 (FIG. 4A and Table 2). The size of this hybridizing band is consistent with the production of a single DNA fragment defined by the EcoRI restriction site at bp 4509 within the T-DNA (FIG. 1) and a potential EcoRI site downstream in the cotton genomic DNA flanking the 3' end of the T-DNA insert. These results confirmed integration of the nos promoter, the nptII coding sequence, and the nos terminator adjacent to the LB region of the T-DNA in event TAM66274. The results shown in FIG. 4A suggest a single copy integration of the T-DNA in event TAM66274. Probe 1 hybridized with the positive control, EcoRI digest of plasmid pART27-LCT66, and produced a hybridizing band of 13.8 kb (FIG. 4A). No hybridizing bands were observed with the EcoRI digest of genomic DNA from non-transgenic cv. Coker 312.

The LB integration pattern of T-DNA in event TAM66274 was further confirmed by an additional Southern blot analysis. Genomic DNA from event TAM66274 was digested with the restriction enzyme KpnI, followed by hybridization with Probe 1 (FIG. 4B). With this restriction enzyme and probe combination, any hybridizing band >4095 bp is considered an integration in the genome (Table 2). A single hybridization band of ~10 kb size was observed in event TAM66274 (FIG. 4B). The size of this hybridizing band is consistent with the production of a single DNA fragment defined by the KpnI restriction site at bp 2666 within the T-DNA (FIG. 1) and a potential KpnI site in the genomic cotton DNA flanking the 3' end of the T-DNA insert. Thus, the results from this Southern blot are consistent with those from the EcoRI/Southern blot (FIG. 4A) showing the LB region of the T-DNA integration at a single locus in event TAM66274. Probe 1 also hybridized with the positive control, KpnI digest of the plasmid pART27-LCT66, and produced a hybridizing band of 16.0 kb (FIG. 4B). The size of this hybridizing band is consistent with the production of a single DNA fragment defined by the single KpnI restriction site at bp 2666 in the plasmid and, therefore, is the complete linearized plasmid pART27-LCT66. Further, no hybridizing bands were observed with Probe 1 for the KpnI digest of genomic DNA from non-transgenic cv. Coker 312.

TABLE 2

LB T-DNA integration analysis.
Size(s) of the expected and observed hybridization bands in event TAM66274.
LB T-DNA integration - event TAM66274

| Restriction enzyme and position | Probe | SEQ ID NO and size (bp) | Expected band (kb) | Observed band (kb) | Expected band for the positive control plasmid (kb) |
|---|---|---|---|---|---|
| EcoRI (4509) | 1 | SEQ ID NO: 8 4528-5439 (912) | >2.3 | ~3.6 | 14.0 |
| KpnI (2666) | 1 | SEQ ID NO: 8 4528-5439 (912) | >4.1 | ~10 kb | 16.0 |

Integration of Internal Genetic Elements of the T-DNA

Results from the RB and LB integration Southern blot analyses using probes corresponding to the T-DNA borders showed single integrations of the ocs terminator region and the nptII cassette in event TAM66274. In order to establish that the genetic elements between these two regions of the T-DNA, along with the RB and LB, were integrated in event TAM66274 as a single T-DNA insert, a separate set of Southern blot analyses was conducted. These Southern blots were conducted following digestion of the genomic DNA with KpnI since this enzyme cuts only once within the T-DNA. Approximately 12 μg of genomic DNA was digested with KpnI and loaded per lane. Positive controls included KpnI digested pART27-LCT66 plasmid at approximately one copy equivalent per cotton genome mixed with 12 μg of genomic DNA extracted from non-transgenic cv. Coker 312. The negative control included genomic DNA from non-transgenic cv. Coker 312. Fragment sizes are shown in kb. The membrane was hybridized with radiolabeled (A) dCS trigger (Probe 14), (B) pdk intron (Probe 15) or (C) AGP (Probe 16). The location of Probes 14, 15, and 16 is shown in FIG. 1. Southern blot analyses conducted following digestion of the genomic DNA are shown in FIG. 5 where the lane marked (+) is the positive control; the lane marked (−) is negative control; and the lane marked 66274 is event TAM66274.

The KpnI restriction site is present at position 2666 bp of the T-DNA, and it delineates the genetic elements adjacent to the RB of the T-DNA, which include the ocs terminator, the dCS Trigger B and the pdk intron, from genetic elements adjacent to the LB of the T-DNA, which include the dCS Trigger A, AGP and the nptII gene cassette. Three different probes (14, 15 and 16) were used to hybridize with individual Southern blots each carrying KpnI digested DNA from event TAM66274 (FIG. 5 and Table 3).

Probe 14 corresponds to the dCS trigger coding sequences and, as expected, showed multiple hybridization bands in the lane containing the genomic DNA from non-transgenic cv. Coker 312 (a dominant band at ~16 kb and less intense lower molecular weight bands at ~8.0 kb, ~3.9 kb and ~3.3 kb). The results from this Southern blot are consistent with the fact that the dCS coding sequence is a member of a multigene family found in the cotton genome, with other members exhibiting high levels of sequence homology. Therefore, hybridizing bands in the non-transgenic cv. Coker 312 lane, which are produced by KpnI restriction digest of the cotton genomic DNA and hybridize with Probe 14, correspond to the multigene family members of the endogenous dCS gene(s) (FIG. 5A). In the event TAM66274 lane, in addition to the hybridizing bands described for non-transgenic cv. Coker 312, there are hybridizing bands of sizes ~4.3 kb and ~10 kb. The ~4.3 kb band is consistent with hybridization of Probe 14 with the dCS Trigger B coding sequence in a DNA fragment produced by the KpnI restriction site at bp 2666 within the T-DNA and a potential KpnI site upstream in the genomic cotton DNA flanking the 5' end of the T-DNA insert. This ~4.3 kb hybridizing band is the same DNA fragment produced by KpnI digest of event TAM66274 DNA which hybridized with Probe 13 (corresponding to the ocs terminator), as shown in FIG. 3B. This result supports the conclusion that the ocs terminator and dCS Trigger B are contiguous in the T-DNA. The ~10.0 kb band is consistent with hybridization of Probe 14 with the dCS Trigger A gene in a DNA fragment produced by the KpnI restriction site at bp 2666 within the T-DNA (FIG. 1) and a potential KpnI site downstream in the genomic cotton DNA flanking the 3' end of the T-DNA insert. The ~10.0 kb hybridizing band is the same DNA fragment produced by KpnI digest of event TAM66274 DNA which hybridized with Probe 1 (corresponding to the nos promoter and part of the nptII gene), as shown in FIG. 4B. This result supports the conclusion that the dCS Trigger A gene and the nptII gene cassette are on the same KpnI digest fragment of the T-DNA as shown in FIG. 1. The positive control lane (non-transgenic cv. Coker 312 DNA spiked with plasmid pART27-LCT66) with Probe 14 showed the same hybridizing bands as the non-transgenic cv. Coker 312 lane (FIG. 5A). This was expected since KpnI digest of the plasmid pART27-LCT66 produces a single hybridizing band of 16.0 kb, which corresponds to a DNA fragment defined by the single KpnI restriction site at bp 2666 in the plasmid and, therefore, is the complete linearized plasmid pART27-LCT66. This hybridizing band co-migrated with the ~16.0 kb band produced by KpnI digest of non-transgenic cv. Coker 312 DNA.

Probe 15 corresponds to the pdk intron, which is located adjacent to the dCS Trigger B coding sequence in plasmid pART27-LCT66, and is at the RB end of the T-DNA delineated by the KpnI restriction site at bp 2666 (FIG. 1). Therefore, KpnI restriction digest of event TAM66274 DNA and hybridized with Probe 15 was expected to yield the same ~4.3 kb band as observed with the same KpnI digest and hybridization with Probes 13 and 14, as described above. This was indeed the case (FIG. 5B), which supports the conclusion that the pdk intron is on the same KpnI digested fragment of the T-DNA as the ocs terminator and dCS Trigger B sequences. Also, as expected, a single hybridizing band of 16.0 kb was observed in the positive control lane, corresponding to the linearized plasmid pART27-LCT66 hybridized with Probe 15, and no hybridizing bands were observed in the non-transgenic cv. Coker 312 lane.

Probe 16 corresponds to the AGP sequence, which is located adjacent to the dCS Trigger A coding sequence in plasmid pART27-LCT66, and is at the LB end of the T-DNA delineated by the KpnI restriction site at bp 2666, as shown in FIG. 1. Therefore, KpnI restriction digest of event TAM66274 DNA hybridized with Probe 16 was expected to yield the same 10.0 kb band as observed with the same KpnI digest and hybridization with Probes 14 and 1, as described above (hybridizing with the dCS Trigger A coding sequence and the nos promoter and part of the nptII coding sequence, respectively). This was indeed the case (FIG. 5C), which supports the conclusion that the AGP sequence is on the same KpnI digest fragment of the T-DNA as the dCS Trigger A sequence and the nptII gene cassette. Several hybridizing bands were observed for the non-transgenic cv. Coker 312 KpnI digest with Probe 16 (~16.0 kb, ~6.5 kb and ~5.5 kb), as shown in FIG. 5C. This was to be expected since the AGP sequence is derived from the cotton α-globulin B gene and the three bands correspond to homeologues in the A and D genomes of cotton. There is 82% sequence homology between the promoters from the two genomes. The positive control lane (non-transgenic cv. Coker 312 DNA spiked with plasmid pART27-LCT66) with Probe 16 showed the same hybridizing bands as the non-transgenic cv. Coker 312 lane. This was expected since KpnI digest of the plasmid pART27-LCT66 produces a single hybridizing band of 16.0 kb that corresponds to a DNA fragment defined by the single KpnI restriction site at bp 2666 in the plasmid and, therefore, is the complete linearized plasmid pART27-LCT66. This hybridizing band co-migrated with the 16.0 kb band produced by KpnI digest of non-transgenic cv. Coker 312 DNA.

Probes 1, 13, 14, 15 and 16 show clearly the contiguous nature of the genetic elements in the integrated T-DNA in event TAM66274 and together show a complete and single copy integration of the T-DNA in event TAM66274.

TABLE 3

Analysis of integration of internal genetic elements of the T-DNA.
Size(s) of the expected and observed hybridization bands in event TAM66274.
Internal Elements integration - event TAM66274

| Restriction enzyme and position | Probe | SEQ ID NO and size (bp) | Expected band(s) (kb) | Observed band(s) (kb) | Expected band for the positive control plasmid (kb) |
|---|---|---|---|---|---|
| KpnI (2666) | 14 | SEQ ID NO: 10 1267-1847 (581) | >2.7, >4.1 | ~4.3, ~10 | 16.0 |
| KpnI (2666) | 15 | SEQ ID NO: 11 1950-2524 (575) | >2.7 | ~4.3 | 16.0 |
| KpnI (2666) | 16 | SEQ ID NO: 12 3340-4479 (1140) | >4.1 | ~10 | 16.0 |

Southern blot analysis using probes adjacent to the RB, LB, and internal to the T-DNA suggested the presence of a complete and single copy of the T-DNA in event TAM66274. The cotton genomic DNA sequences flanking the RB and LB were determined by HE-TAIL PCR (see Tan, H. Q. and Singh, J. (2011) High-efficiency thermal asymmetric interlaced (HE-TAIL) PCR for amplification of Ds transposon insertion sites in barley. *Journal of Plant Molecular Biology and Biotechnology* 2: 9-14.) followed by DNA sequencing of the amplified products. Results of the flanking sequence analysis identified terminal deletion of the entire 25 bp RB T-DNA repeat plus three bp of the RB overdrive and an 18 bp deletion of the LB T-DNA repeat occurred during T-DNA integration in event TAM66274. No genetic elements from the backbone DNA of the plasmid were integrated in the even TAM66274 genome. The remainder of the T-DNA border regions inserted in event TAM66274 are identical to the pART27-LCT66 plasmid.

TABLE 4

Description of genetic elements in T-DNA insert (6714 bp) in event TAM66274.

| Genetic Element (GE) | Location in T-DNA insert in TAM66274 | GE Size (bp) | Description |
|---|---|---|---|
| Right border-flanking sequence | | 1,035 | Cotton genomic DNA flanking the right border of the transgene insert in TAM66274. |
| | | | Transgene insert start |
| Right border overdrive element | 29-177 | 149 | Sequences flanking the right border repeat in the T-DNA |
| Intervening sequence | 178-441 | 264 | Sequences of LacZ promoter and 5' truncated LacZ' gene from pGEM-5Zf(−) vector (Promega, Madison, WI) used for cloning purpose. |
| mcs + ocs terminator | 442-1230 | 789 | Multiple cloning site sequences + 3' UTR terminator of octopine synthase gene derived from *Agrobacterium tumefaciens* |
| Intervening sequence | 1231-1243 | 13 | Sequence used for DNA cloning. |
| dCS Trigger B | 1244-1847 | 604 | Trigger B of the δ-cadinene synthase gene from *Gossypium hirsutum* |
| Intervening sequence | 1848-1891 | 44 | Sequence used for DNA cloning. |
| pdk intron | 1892-2635 | 744 | Intron of the pyruvate orthophosphate di kinase gene from *Flaveria trinervia* |
| Intervening sequence | 2636-2679 | 44 | Sequence used for DNA cloning. |
| dCS Trigger A | 2680-3283 | 604 | Trigger A of the δ-cadinene synthase gene from *Gossypium hirsutum* |
| Intervening sequence | 3284-3339 | 56 | Sequence used for DNA cloning. |
| AGP | 3340-4485 | 1146 | Promoter and 5' UTR derived from the α-globulin B gene of *Gossypium hirsutum* |
| Intervening sequence | 4486-4790 | 305 | Sequences of multiple cloning sites from pHANNIBAL (Wesley et al., 2001), 3' truncated LaZ' gene and multiple cloning sites from pGEM-5Zf(−) vector (Promega, Madison, WI) used for cloning purposes. |
| nos promoter | 4791-4974 | 184 | Nopaline synthase promoter derived from *Agrobacterium tumefaciens* |
| Partial nos gene | 4975-5025 | 51 | Partial sequence of the 5' end of the nopaline synthase gene coding sequence derived from *Agrobacterium tumefaciens* |
| nptII gene | 5026-5796 | 771 | Neomycin phosphotransferase II gene derived from *Escherichia coli* Tn5, which confers resistance to kanamycin |
| Intervening sequence | 5797-5969 | 173 | Partial sequence of the 5' end of the bleomycin resistance gene coding sequence derived from |
| Intervening sequence | 5970-6400 | 431 | Partial sequence of the 3' end of the nopaline synthase gene coding sequence derived from *Agrobacterium tumefaciens* (An et al., 1985, 1988). |
| nos terminator | 6401-6675 | 275 | Nopaline synthase terminator and poly(A) signal |
| Intervening sequence | 6676-6735 | 60 | Sequence used for DNA cloning |
| Partial T-DNA left border repeat | 6736-6742 | 7 | DNA region from *Agrobacterium tumefaciens* containing the left border sequence used for transfer of the T-DNA |
| | | | Transgene insert end |
| Left border-flanking sequence | | 1152 | Cotton genomic DNA flanking the left border of the transgene insert in TAM66274. |

Figure 6:
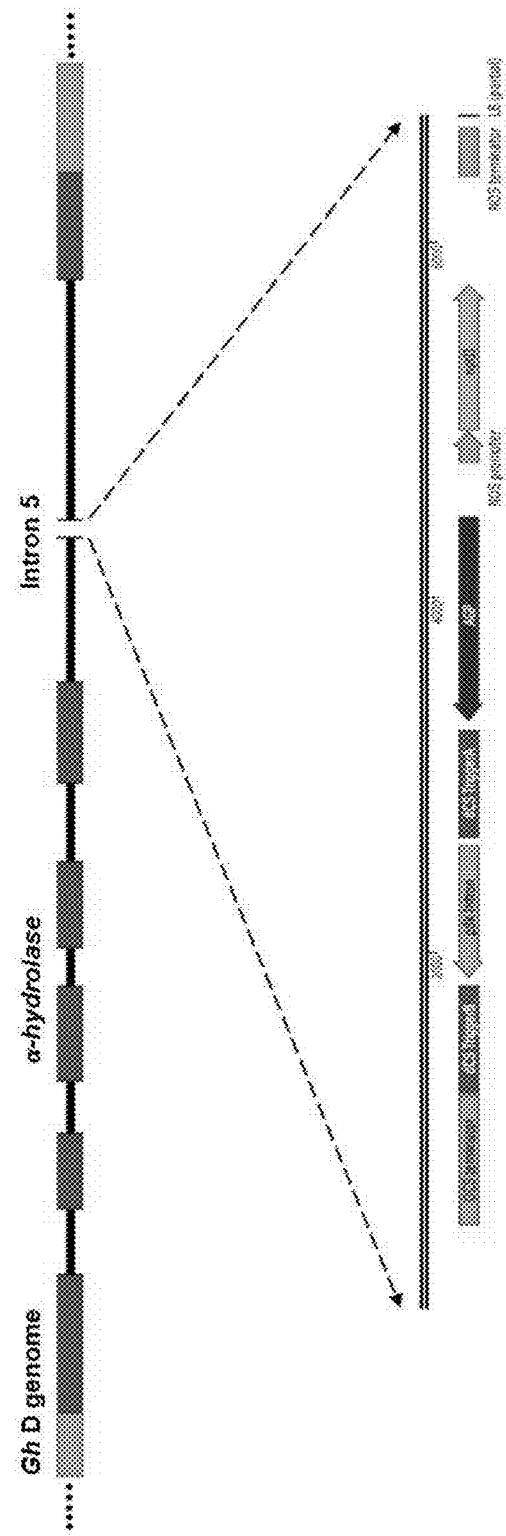
FIG. 6 shows a diagrammatic representation of the T-DNA insertion site in event TAM66274. Insertion of the transgene caused a deletion of 44 bases in the intron of the α-hydrolase gene in event TAM66274.

The T-DNA genomic flanking sequences were used to conduct a BLAST search of the *G. hirsutum* genomic sequence (Li, F., Fan, G., Lu, C., et al. (2015) Genome sequence of cultivated upland cotton (*Gossypium hirsutum* TM-1) provides insights into genome evolution. Nature Biotechnology 33: 524-530.; www.cottongen.org), which indicated that the T-DNA insertion in event TAM66274 had occurred within the last intron of an α-hydrolase gene. This was further confirmed by searching the Phytozome database (phytozome.jgi.doe.gov/pz/portal.html#!search?show=BLAST&method=Org_Graimondii) for the diploid cotton, *G. raimondii*. Primers were designed based on the RB and LB T-DNA flanking sequence and were used to conduct PCR on non-transgenic cv. Coker 312 genomic DNA. The amplicon generated was sequenced and confirmed that during the T-DNA insertion in event TAM66274, 44 bp of the cotton genomic DNA was deleted in the intron of the α-hydrolase gene. The BLAST search also showed that the T-DNA in event TAM66274 was inserted within the last intron of an α-hydrolase gene, at 364 bases from the 5' end of the intron-exon junction (FIG. 6). According to genomic sequence data for *G. hirsutum* in the CottonGen database, this gene is located on Chromosome D7.

Figure 7:
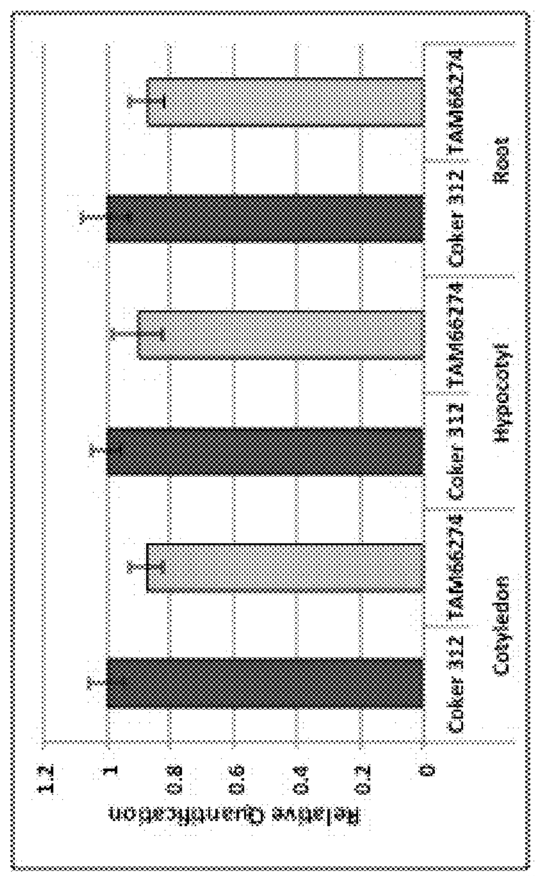
FIG. 7 shows qRT-PCR results for expression of the putative α-hydrolase gene in various tissues in plants comprising event TAM66274 and in non-transgenic cv. Coker 312. The relative quantification (RQ) values for α-hydrolase expression in non-transgenic cv. Coker 312 and plants comprising event TAM66274 are presented in the graph. Two biological replicates and three technical replicates were used for the qRT-PCR analyses of the seedling tissues. The top and bottom of the error bars represent RQ max and RQ min values, respectively. Gh Histone 3A was used as an internal control to normalize the expression of α-hydrolase gene.
Figure 8:
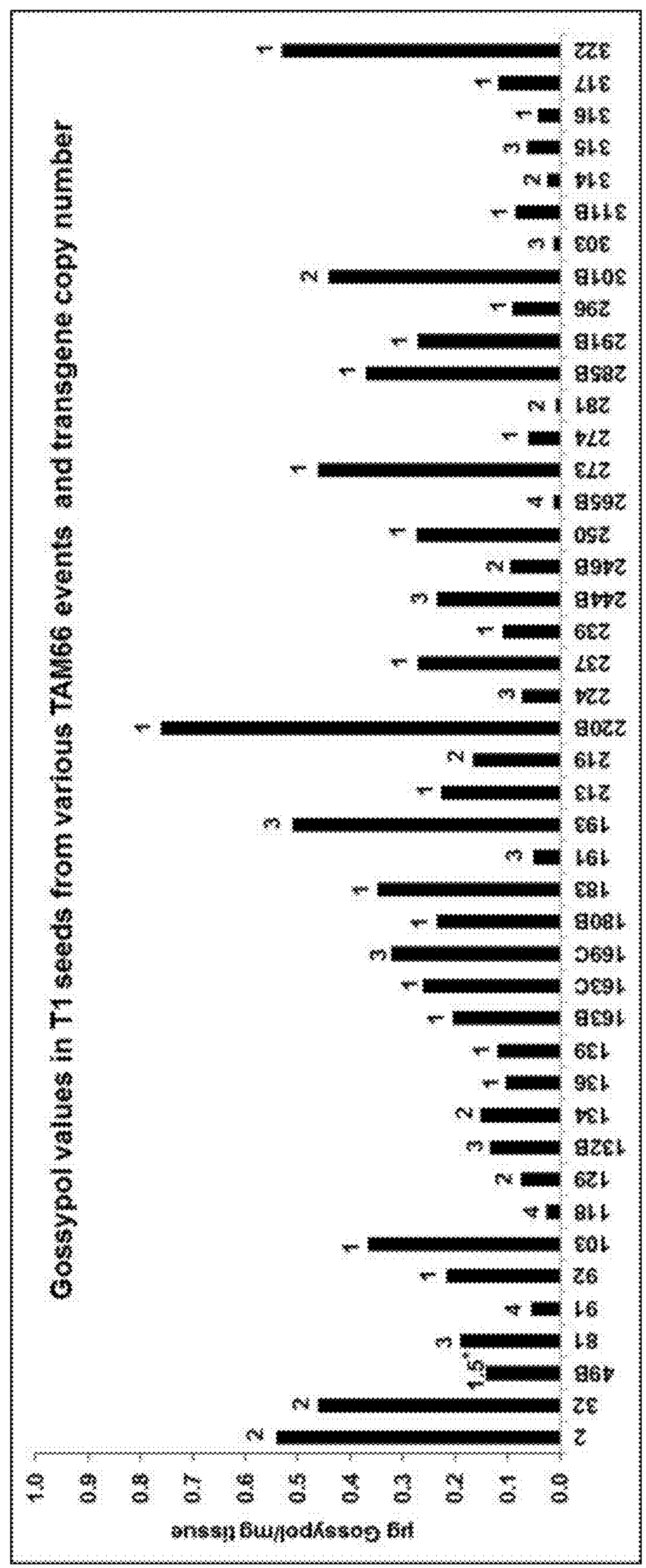
FIG. 8 shows gossypol levels (μg gossypol/mg seed kernel tissue) in T1 seeds (excluding null segregants) of various events generated by *Agrobacterium tumefaciens*-mediated transformation of cotton tissues from non-transgenic cv. Coker 312 using plasmid pART27-LCT66. Southern blot analyses were performed and the transgene copy numbers determined are shown above individual bars. As shown, event TAM66274 yielded 1 copy and low gossypol seed values. Event 6649B was found to have an additional, partial transgene copy integration that was not revealed in the early Southern blot analysis.

Since the integration of the T-DNA in event TAM66274 occurred in an intron of a putative α-hydrolase gene, it is unlikely to affect its expression. Nevertheless, qRT-PCR analysis was performed to determine the effect of T-DNA integration on the mRNA expression of the putative α-hydrolase gene. Primers designed from the 3' UTR region of the putative α-hydrolase gene were such that these will amplify only the desired gene and not its close homologs/other gene family members. The qRT-PCR analysis was performed on the cotyledons, roots and hypocotyl of three-day-old seedlings comprising event TAM66274 and non-transgenic cv. Coker 312. No major differences were observed in the levels of mRNA expression of the putative α-hydrolase gene between samples comprising event TAM66274 and non-transgenic cv. Coker 312. FIG. 7 shows the qRT-PCR results for expression of the putative α-hydrolase gene in various tissues comprising event TAM66274 and non-transgenic cv. Coker 312. Two biological replicates and three technical replicates were used for the qRT-PCR analyses of the seedling tissues. The top and bottom of the error bars represent relative quantification (RQ) max and RQ min values, respectively. Gh Histone 3A was used as an internal control to normalize the expression of α-hydrolase gene. Furthermore, phenotypic, agronomic and seed composition evaluations of tissue comprising event TAM66274 and non-transgenic cv. Coker 312 confirmed that integration of the T-DNA in the intron of the α-hydrolase gene had no effect on plant metabolism or growth and development.

In summary, the T-DNA insert in event TAM66274 was characterized using a combination of Southern blots and HE-TAIL PCR analyses. Southern blots used a combination of EcoRI restriction digests, KpnI restriction digests, and probes to the ocs terminator adjacent to the RB of the T-DNA and probes to parts of the nptII gene cassette adjacent to the LB of the T-DNA. Results showed single inserts of the ocs terminator and nptII gene cassette in event TAM66274. Additional Southern blot analyses conducted following digestion of genomic DNA with KpnI and hybridization with probes corresponding to dCS trigger sequence, pdk intron and AGP (internal genetic elements within the T-DNA) further confirmed the integrity of the T-DNA insert and its integration as a single copy in event TAM66274. HE-TAIL PCR analysis also showed that the entire RB repeat was not integrated in the plant genome, and only seven nucleotides from the LB repeat were included in the T-DNA insert in event TAM66274. No genetic elements from the backbone of the pART27-LCT66 plasmid were integrated in event TAM66274 as shown by Southern blots using EcoRI restriction digest and overlapping probes to the entire backbone of the plasmid. Analysis of cotton genomic DNA flanking the T-DNA insert in event TAM66274 showed that the T-DNA integration occurred in an intron of a putative α-hydrolase gene. However, qRT-PCR analysis showed that there was no impact on mRNA expression from this gene in tissue comprising event TAM66274 compared to non-transgenic cv. Coker 312. Also, companion studies on phenotypic, agronomic, morphological and cotton seed composition showed that plants comprising event TAM66274 and non-transgenic cv. Coker 312 are comparable with respect to these parameters, and confirms that integration of the T-DNA insert in the intron of the α-hydrolase gene had no effect on plant metabolism or growth and development.

Example 3

Gossypol Levels in Event TAM66274 Containing Seeds

Gossypol exists as either free or bound in the plant. The free form of gossypol is the toxic form of the compound. Due to steric hindrance between the functional groups of the molecule at the bond connecting the two naphthyl rings (atropisomerism), gossypol has both (+) and (−) isomers. In the seed of the commercially important varieties of Upland cotton grown in the United States, the predominant isomer is (+) gossypol. Gossypol is physiologically active with the (−) isomer appearing to be more active than the (+) isomer. Therefore, it is important to know the relative amounts of each of the isomers. Accordingly, total and free gossypol were measured in samples, as well as the isomers of gossypol. Furthermore, total gossypol was measured by two different methods, the aniline and the HPLC methods. The aniline method is a relatively fast method used for measuring gossypol in plant tissues, and is commonly used in the cotton industry. However, because the method also detects impurities and other terpenoids in addition to gossypol, the method can overestimate levels of gossypol in specific plant tissues. The HPLC method measures each terpenoid separately in plant tissues, so is a more accurate method for measuring gossypol in plant tissues. In the case of cotton seed, gossypol is the predominant terpenoid, so there is a good correlation between the aniline and HPLC methods for measuring gossypol.

Cotton seed samples comprising event TAM66274 and non-transgenic cv. Coker 312 harvested from 2014 and 2015 field trials were analyzed for total and free gossypol content, as well as for levels of the gossypol isomers. The means and ranges of levels of the gossypol fractions in cotton seed comprising event TAM66274 and non-transgenic cv. Coker 312, as well as the ranges published in the ILSI Crop Composition Database and in the literature, are shown in Tables 5 and 6. These data show that the ULGCS trait was expressed in event TAM66274 comprising plants and levels of all gossypol fractions in event TAM66274 comprising plants were statistically significantly reduced compared to the levels in non-transgenic cv. Coker 312 in cotton seed harvested from both 2014 and 2015 field trials. Levels of total gossypol in cotton seed comprising event TAM66274 harvested from 2014 and 2015 field trials were 440 ppm and 420 ppm on a dry weight basis, respectively, compared to levels of 9,630 ppm and 9,410 ppm in cotton seed of non-transgenic cv. Coker 312 harvested from the same field trials, when using the aniline method of measurement. Total gossypol levels in cotton seed comprising event TAM66274 harvested from 2014 and 2015 field trials were 4.57% and 4.46% of levels in non-transgenic cv. Coker 312, respectively. When total gossypol levels were compared between event TAM66274 comprising seed and non-transgenic cv. Coker 312 using the HPLC method of measurement, total gossypol levels in event TAM66274 comprising seed harvested from 2014 and 2015 field trials were 370 ppm and 300 ppm on a dry weight basis, respectively, compared to levels of 10,300 ppm and 10,000 ppm in cotton seed of non-transgenic cv. Coker 312 harvested from the same field trials. Total gossypol levels in cotton seed comprising event TAM66274 harvested from 2014 and 2015 field trials were 3.61% and 3.30% of levels in non-transgenic cv. Coker 312, respectively. As described above, the HPLC method gives less experimental error and is more accurate than the aniline method for measuring levels of gossypol in cotton seed. Therefore, total gossypol levels for the treatments measured by HPLC are considered more accurate than the aniline method as presented in Table 5. Further, the ultra-low levels of gossypol in cotton seed comprising event TAM66274 were confirmed from total gossypol values calculated from the sum of levels of the isomers which were measured by an HPLC method (total gossypol levels of 256 and 283 ppm for cotton seed comprising event TAM66274 harvested from 2014 and 2015 field trials, respectively, compared to 6,713 ppm and 6,932 ppm for non-transgenic cv. Coker 312 harvested from the same field trials) (Table 6).

The ULGCS trait did not have any meaningful effect on the relative levels of free and bound gossypol in the cotton seed, but the percent of the free form of the compound (which is the biologically active form) in total gossypol tended to be lower in event TAM66274 comprising seed compared to non-transgenic cv. Coker 312. Levels of free gossypol relative to total gossypol levels (levels compared using values from the aniline assay) were 80.7% for non-transgenic cv. Coker 312 and 68.2% for event TAM66274 comprising seed for cotton seed from 2014 field trials, and 88.2% for non-transgenic cv. Coker 312, 61.9% for seed comprising event TAM66274 for cotton seed harvested from 2015 field trials (Table 5). Furthermore, the ULGCS trait did not have any meaningful effect on the relative levels of the (+)-gossypol and (−)-gossypol isomers in the cotton seed. Ratios of levels of the (+)-gossypol isomer to the (−)-gossypol isomer were 1.38 for non-transgenic cv. Coker 312 and 1.36 for seed comprising event TAM66274 for cotton seed from 2014 field trials, and were 1.54 for non-transgenic cv. Coker 312 and 1.30 for seed comprising event TAM66274 for cotton seed harvested from 2015 field trials (Table 6).

In summary, the data presented in Tables 5 and 6 show that the ULGCS trait was expressed in seed comprising event TAM66274 and, as expected, the level of total gossypol in cotton seed comprising event TAM66274 was reduced to approximately 3% of levels in the non-transgenic cv. Coker 312 cotton seed. Using the more accurate and precise HPLC method for measurement, mean total gossypol levels in cotton seed comprising event TAM66274 harvested from both 2014 and 2015 field trials were below the maximum allowable level of 450 ppm considered safe for modified cotton seed products in foods for human consumption and below 400 ppm allowed in low-gossypol cotton seed meal used as animal feed. Also, the ULGCS trait did not have any meaningful effect on either the relative levels of free and bound gossypol in cotton seed, or on relative levels of (+) and (−) gossypol isomers in the cotton seed. As shown in Table 5, the comparison of the total and free gossypol composition of cotton seed comprising event TAM66274 and non-transgenic cv. Coker 312 grown in three U.S. field locations in 2014, and five U.S. field locations in 2015. Total gossypol was measured by two different methods, the aniline method and by HPLC. Total and free gossypol levels for each treatment are presented as the means, standard error of the means, and the range across field locations, and levels are compared with the range of levels reported in the ILSI Crop Composition Database (ILSI, 2016), and with ranges of levels reported in the literature for cotton seed from conventional cotton varieties. Gossypol levels are expressed as a percent on a dry weight basis.

TABLE 5

Cotton seed total and free gossypol composition.

| | Analytes | | |
|---|---|---|---|
| Treatments | Total Gossypol (%) (by aniline) | Total Gossypol (%) (by HPLC) | Free Gossypol (%) (by aniline) |
| | 2014 Studies Means (±S.E.M., Ranges) | | |
| Coker 312 | 0.963 ± 0.009 (0.930-0.988) | 1.03 ± 0.035 (0.880-1.14) | 0.777 ± 0.004 (0.763-0.789) |
| TAM66274 | 0.044 ± 0.009 (0.040-0.050) | 0.037 ± 0.035 (0.028-0.048) | 0.030 ± 0.004 (0.027-0.033) |
| Significance (p-value) of TAM66274 vs. Coker 312 | 0.0001† | 0.0001† | 0.0001† |
| Treatments | 2015 Studies Means (±S.E.M., Ranges) | | |
| Coker 312 | 0.941 ± 0.025 (0.781-1.04) | 1.00 ± 0.042 (0.731-1.28) | 0.830 ± 0.020 (0.701-0.905) |
| TAM66274 | 0.042 ± 0.025 (0.035-0.051) | 0.030 ± 0.002 (0.018-0.047) | 0.026 ± 0.020 (0.021-0.029) |
| Significance (p-value) of TAM66274 vs. Coker 312 | 0.0001† | 0.0001† | 0.0001† |
| ILSI CCDB range of analyte values | | | |
| Min | 0.350 | N.R. | 0.384 |
| Max | 1.61 | N.R. | 1.42 |
| Literature range of analyte values | | | |
| Min | 0.550[a] | N.R. | 0.492[b] |
| Max | 1.61[c] | N.R. | 1.41[c] |

†Mean analyte values for TAM66274 compared to values for Coker 312 are statistically significantly different at $P < 0.05$.
Literature ranges of analyte values: [a]Bertrand et al. (2005); [b]Rudgers (2013); [c]Arackal et al. (2012).
N.R. Not reported.

As shown in Table 6, a comparison of the gossypol isomers and total gossypol composition of cotton seed from event TAM66274 and non-transgenic cv. Coker 312 grown in three U.S. field locations in 2014, and five U.S. field locations in 2015. Total gossypol content of the cotton seed was calculated as the sum of the content of the (+)- and (−)-gossypol isomers. Levels of the gossypol isomers were measured by HPLC. Levels of the gossypol isomers and total gossypol for each treatment are presented as the means, standard error of the means, and the range across field locations. Gossypol levels are expressed on a dry weight basis.

TABLE 6

| Cotton seed (+)-and (−)-gossypol isomers and total gossypol composition. | | | |
|---|---|---|---|
| | Analytes | | |
| Treatments | (+)-gossypol (μg/g) | (−)-gossypol (μg/g) | Total gossypol (μg/g) |
| | 2014 Studies Means (±S.E.M., Ranges) | | |
| Coker 312 | 3,893 ± 37 (3,800-4,010) | 2,820 ± 43 (2,670-2,920) | 6,713 ± 76 (6,470-6,930) |
| TAM66274 | 148 ± 37 (141-158) | 109 ± 43 (104-118) | 256 ± 76 (245-276) |
| Significance (p-value) of TAM66274 vs. Coker 312 | 0.0001† | 0.0001† | 0.0001† |
| Treatments | 2015 Studies Means (+S.E.M., Ranges) | | |
| Coker 312 | 4,204 ± 86 (3,870-4,600) | 2,728 ± 88 (2,220-3,090) | 6,932 ± 170 (6,090-7,610) |
| TAM66274 | 160 ± 86 (122-192) | 123 ± 88 (97.6-146) | 283 ± 170 (220-338) |
| Significance (p-value) of TAM66274 vs. Coker 312 | 0.0001† | 0.0001† | 0.0001† |
| ILSI CCDB range of analyte values | | | |
| Min | N.R. | N.R. | N.R. |
| Max | N.R. | N.R. | N.R. |
| Literature range of analyte values | | | |
| Min | N.R. | N.R. | N.R. |
| Max | N.R. | N.R. | N.R. |

Example 4

Terpenoid Analyses in Seed Kernels, Vegetative and Reproductive Tissues of Event TAM66274

To assess the specificity, efficacy and stability of the ULGCS phenotype under field conditions, the levels of gossypol and related plant-defense terpenoids were measured in the seed and six non-seed tissues comprising event TAM66274 and derived from non-transgenic cv. Coker 312. Plants were grown at the Texas A&M University Field Laboratory (Sommerville, Tex.) during the 2012 and 2015 growing seasons.

Six different tissues (leaves, bracts, terminal ends of axillary branches, floral buds, petals and 2-day old bolls) were harvested 8-10 weeks after sowing, freeze-dried and ground to a fine powder. Terpenoid analyses were performed on these samples and cotton seed kernels using HPLC, following the methods described by Stipanovic, R. D., Altman, D. W., Begin, D. L., Greenblatt, G. A. and Benedict, J. H. (1988) Terpenoid aldehydes in upland cottons: Analysis by aniline and HPLC methods. *Journal of Agricultural and Food Chemistry* 36: 509-51 and Benson, C. G., Wyllie, S. G., Leach, D. N., Mares, C. L. and Fitt, G. P. (2001) Improved method for the rapid determination of terpenoid aldehydes in cotton. *Journal of Agricultural and Food Chemistry* 49: 2181-2184. Briefly, the finely ground green tissue/petal sample (approximately 100 mg) was extracted by ultrasonication (10 min) in 5 ml of solvent containing acetonitrile/water/phosphoric acid (80:20:0.1) in a 15 ml polypropylene tube. Following centrifugation at 2800×g for 5 min, a 50-μl fraction of the extract was analyzed on an Agilent Technologies (Palo Alto, Calif.) 1200 liquid chromatograph, equipped with a diode array detector for compound spectral identification as described in Stipanovic et al., 1988 and Sunilkumar, G., Campbell, L. M., Puckhaber, L., Stipanovic, R. D. and Rathore, K. S. (2006) Engineering cottonseed for use in human nutrition by tissue specific reduction of toxic gossypol. *Proceedings of National Academy of Sciences USA* 103: 18054-18059.

A slightly different procedure was used for extracting terpenoids from seeds. Twelve to 15 seeds from each plant were dehulled, and the kernels were ground to a fine powder. Approximately, 500 mg of ground seed was mixed with 50 ml of solvent containing ethanol/ether/water/glacial acetic acid (59:17:24:0.2). The suspension was agitated on a shaker at room temperature for 1 h to facilitate extraction of terpenoids. The final sample volume was adjusted to 50 ml to account for evaporation and centrifuged for 15 min at 2800×g. A 50-μl fraction of the extract was analyzed using the HPLC as described above.

Gossypol, hemigossypolone, and heliocides H1-H4 were reported as μg/mg dry weight of tissue (mean±SE; n=3 in 2012; n=4 in 2015). The results demonstrate the tissue-specificity of the α-globulin promoter that drives RNAi-mediated suppression of dCS in seed tissues while leaving levels of gossypol and related terpenoids unchanged in non-seed tissue, as shown in Table 7.

TABLE 7

| Levels of gossypol and related terpenoids. | | | | | |
|---|---|---|---|---|---|
| | | 2012 | | 2015 | |
| | | Coker 312 | 66-274 | Coker 312 | 66-274 |
| Bracts | G | 0.11 (±0.01) | 0.17 (±0.01) | 0.09 (±0.01) | 0.08 (±0.00) |
| | HGQ | 0.29 (±0.04) | 0.60 (±0.05) | 0.13 (±0.03) | 0.17 (±0.01) |
| | H1-H4 | 2.37 (±0.15) | 2.2 (±0.06) | 1.31 (±0.25) | 1.17 (±0.07) |
| Floral buds | G | 2.07 (±0.25) | 1.73 (±0.22) | 4.32 (±0.34) | 2.56 (±0.12) |
| | HGQ | 1.02 (±0.07) | 1.06 (±0.11) | 0.50 (0.05) | 0.37 (±0.01) |
| | H1-H4 | 3.3 (±0.24) | 2.55 (±0.30) | 1.45 (±0.06) | 1.22 (±0.07) |
| Terminal part of axillary branch | G | 0.51 (±0.06) | 0.77 (±0.01) | 0.85 (±0.03) | 0.72 (±0.05) |
| | HGQ | 1.31 (±0.12) | 1.52 (±0.04) | 1.93 (±0.05) | 1.78 (±0.18) |
| | H1-H4 | 2.12 (±0.18) | 2.66 (±0.11) | 3.17 (±0.18) | 2.66 (±0.22) |
| Leaves | G | 0.95 (±0.09) | 1.01 (±0.10) | 0.757 (±0.02) | 0.84 (±0.06) |
| | HGQ | 5.38 (±0.39) | 4.48 (±0.32) | 2.315 (±0.4) | 3.74 (±0.22) |
| | H1-H4 | 5.67 (±0.50) | 3.32 (±0.34) | 1.42 (±0.28) | 1.83 (±0.1) |

TABLE 7-continued

| Levels of gossypol and related terpenoids. | | | | | |
|---|---|---|---|---|---|
| | | 2012 | | 2015 | |
| | | Coker 312 | 66-274 | Coker 312 | 66-274 |
| 2-day bolls | G | 0.90 (±0.08) | 0.84 (±0.05) | 1.34 (±0.09) | 0.82 (±0.06) |
| | HGQ | 4.30 (±0.18) | 3.69 (±0.24) | 4.77 (±0.24) | 3.87 (±0.20) |
| | H1-H4 | 8.4 (±0.30) | 6.46 (±0.37) | 9.69 (±0.4) | 6.7 (±0.25) |
| Petals | G | 2.96 (±0.28) | 3.00 (±0.06) | 4.5 (±0.25) | 3.8 (±0.17) |
| Seed kernel | G | 8.12 (±0.02) | 0.16 (±0.00) | 11.2 (±1.12) | 0.32 (±0.04) |

G: Gossypol; HGQ: Hemigossypolone; H1-H4: Heliocides. Note that the predominant terpenoid in the seed and flower petal glands is gossypol.

Example 5

Seed Specific Trait Characterization

Quantitative, fluorometric β-glucuronidase (GUS) analysis revealed that AGP became active at 15 days post-anthesis (dpa), during the cotyledon expansion stage in the developing embryo. Its activity quickly increased thereafter and remained high until embryo maturation. In contrast, there was no detectable GUS activity in the stem, leaf, root, pollen, and floral bud tissues of the transgenic cotton plants. These analyses confirmed the seed-specificity of AGP in cotton. Moreover, AGP remained inactive in the foliage of cotton plants even under extreme water stress conditions. These results suggested that AGP-based seed-specificity of the ULGCS trait would be maintained under field conditions where plants are likely to experience water stress. This critical test was performed to determine the exclusivity of the AGP since some seed-specific promoters are known to exhibit leaky activity in the foliage under water stress.

In seven years of field trials at Texas A&M University, there were no significant changes in the terpenoid profile in non-seed tissues of multiple ULGCS events under the control of AGP, including TAM66274, compared to non-transgenic cv. Coker 312. Thus, the ULGCS plants retain terpenoid-based defenses under field conditions. This was verified in field studies with plants comprising event TAM66274 and non-transgenic cv. Coker 312, which detected no difference in susceptibility to insects or diseases between the two treatments.

Example 6

Deposit of Representative Seed of Event TAM66274

A deposit of a representative sample of cotton seed comprising event TAM66274 has been made according to the Budapest Treaty with the American Type Culture Collection (ATCC) having an address at 10801 University Boulevard, Manassas, Va. USA, Zip Code 20110. The ATCC Patent Deposit Designation (accession number) for seeds comprising event TAM66274 is PTA-124218 and the date of deposit was Jun. 2, 2017. Access to the deposits will be available during the pendency of the application to the Commissioner of Patents and Trademarks and persons determined by the Commissioner to be entitled thereto upon request. The deposit will be maintained in the depository for a period of 30 years, or 5 years after the last request, or for the effective life of the patent, whichever is longer, and will be replaced as necessary during that period.

Having illustrated and described the principles of the invention, it should be apparent to persons skilled in the art that the invention can be modified in arrangement and detail without departing from such principles. We claim all modifications that are within the spirit and scope of the appended claims.

We claim:

1. A recombinant DNA molecule comprising a nucleotide sequence selected from the group consisting of SEQ ID NO:1-4, and complements thereof.

2. The recombinant DNA molecule of claim 1, wherein the recombinant DNA molecule comprises SEQ ID NO:3 and is formed by the insertion of a heterologous nucleic acid molecule into the genomic DNA of a cotton plant or cell.

3. The recombinant DNA molecule of claim 1, wherein said DNA molecule is derived from a transgenic cotton plant comprising event TAM66274, a representative sample of seed comprising cotton event TAM66274 having been deposited under ATCC Accession No. PTA-124218.

4. The recombinant DNA molecule of claim 3, wherein said DNA molecule is in a cotton plant, plant cell, seed, plant part, or commodity product and wherein the DNA molecule comprises the sequence of SEQ ID NO:3.

5. The recombinant DNA molecule of claim 1, wherein said DNA molecule is an amplicon diagnostic for the presence of DNA derived from event TAM66274.

6. A transgenic cotton plant, seed, cell, or plant part thereof comprising the recombinant DNA molecule of claim 3 wherein the recombinant DNA molecule comprises the sequence of SEQ ID NO:3.

7. The transgenic cotton seed of claim 6, wherein said seed exhibits reduced levels of gossypol relative to a seed lacking said recombinant DNA molecule.

8. The transgenic cotton plant, seed, cell, or plant part thereof of claim 6, the genome of which produces an amplicon comprising a DNA molecule diagnostic for event TAM66274, when tested in a DNA amplification method.

9. A cotton plant, seed, cell or plant part thereof comprising event TAM66274, a representative sample of seed comprising event TAM66274 having been deposited under ATCC Accession No. PTA-124218.

10. The cotton plant, seed, cell or part thereof of claim 9, wherein said cotton plant or seed is a hybrid having at least one parent comprising cotton event TAM66274.

11. A nonliving plant material or microorganism comprising the recombinant DNA molecule of claim 3 wherein the recombinant DNA molecule comprises the sequence of SEQ ID NO:3.

12. The nonliving plant material or microorganism of claim 11, defined as a plant cell.

13. A commodity product comprising the recombinant DNA molecule of claim 3 wherein the recombinant DNA molecule comprises the sequence of SEQ ID NO:3.

14. The recombinant DNA molecule of claim 1, wherein the recombinant DNA molecule comprises SEQ ID NO:1.

15. The recombinant DNA molecule of claim 1, wherein the recombinant DNA molecule comprises SEQ ID NO:2.

16. The recombinant DNA molecule of claim 1, wherein the recombinant DNA molecule comprises SEQ ID NO:3.

17. The recombinant DNA molecule of claim 1, wherein the recombinant DNA molecule comprises SEQ ID NO:4.

* * * * *